US007837998B2

(12) United States Patent
Lallatin et al.

(10) Patent No.: US 7,837,998 B2
(45) Date of Patent: Nov. 23, 2010

(54) ANTI-CANCER ACTIVITY OF AN ANTI-THYMIDINE KINASE MONOCLONAL ANTIBODY

(76) Inventors: Nathaniel Lallatin, c/o Jerry Lallatin 226 W. 2230 North, Suite 100, Provo, UT (US) 84604; Kim L. O'Neill, 1671 N. 1670 West, Provo, UT (US) 84604

( * ) Notice: Subject to any disclaimer, the term of this patent is extended or adjusted under 35 U.S.C. 154(b) by 83 days.

(21) Appl. No.: 11/134,854

(22) Filed: May 20, 2005

(65) Prior Publication Data

US 2006/0039914 A1 Feb. 23, 2006

Related U.S. Application Data

(60) Provisional application No. 60/573,429, filed on May 21, 2004.

(51) Int. Cl.
*A61K 31/522* (2006.01)
*A61K 31/7072* (2006.01)
*A61K 31/7076* (2006.01)
*A61K 38/16* (2006.01)
*A61K 39/395* (2006.01)

(52) U.S. Cl. .................. 424/155.1; 514/2; 514/263.2; 514/269; 514/49

(58) Field of Classification Search .............. 424/155.1; 514/2, 263.2, 269, 49
See application file for complete search history.

(56) References Cited

U.S. PATENT DOCUMENTS

| 4,317,877 | A |   | 3/1982  | Balis et al.            |
|-----------|---|---|---------|-------------------------|
| 4,474,893 | A |   | 10/1984 | Reading                 |
| 4,722,899 | A |   | 2/1988  | Hamaoka et al.          |
| 4,816,567 | A |   | 3/1989  | Cabilly et al.          |
| 5,476,996 | A |   | 12/1995 | Wilson et al.           |
| 5,514,548 | A |   | 5/1996  | Krebber et al.          |
| 5,698,409 | A | * | 12/1997 | O'Neill ........... 435/7.23 |
| 5,869,045 | A |   | 2/1999  | Hellstrom et al.        |
| 6,083,707 | A |   | 7/2000  | Eriksson et al.         |
| 6,331,415 | B1 |  | 12/2001 | Cabilly et al.          |
| 6,372,217 | B1 |  | 4/2002  | Uckum                   |
| 2003/0148410 | A1 | * | 8/2003 | Berger et al. ......... 435/7.23 |
| 2006/0039914 | A1 |   | 2/2006 | Lallatin et al.         |
| 2007/0003990 | A1 | * | 1/2007 | Schlegel et al. ........ 435/7.23 |

FOREIGN PATENT DOCUMENTS

| EP | 0042482 | 12/1981 |
| EP | 0255431 | 10/1991 |
| EP | 0454478 | 10/1991 |
| WO | 9306213 | 4/1993 |
| WO | WO 95/29192 | 11/1995 |
| WO | 9708320 | 3/1997 |

OTHER PUBLICATIONS

Search results from ATCC website for "CB100" and "PTA—6704" (pp. 1-2).*
Fundamental Immunology 242 (William E. Paul, M.D. ed., 3d ed. 1993).*
Jain, Scientific American Jul. 1994 pp. 58-65.*
Chatterjee et al., Cancer Immunol. Imunother., 38:75-82, 1994.*
Dermer, Biotechnology 12: 320, 1994.*
Gura et al., Science vol. 278:1041-1042 (Nov. 1997).*
Seaver, 1994; Genetic Engineering vol. 14(14):10 and 21.*
He et al. Cell Prolif. 35(2):69-81 (2002).*
ATCC website search of HB11432 (pp. 1-2).*
ATCC website search of HB11433 (pp. 1-2).*
ATCC website search of HB11434 (pp. 1-2).*
Voskoglou-Nomikos (Clin. Can. Res. 9:4227-4239 (2003)).*
Dennis (Nature 442:739-741 (2006)).*
Cespdes et al. (Clin. Transl. Oncol. 8(5):318-329 (2006)).*
Salfeld (Nature Biotech. 25(12);1369-1372 (2007)).*
Fujimori et al. (J. Nuc. Med. 31:1191-1198 (1990)).*
Beckman et al. (Can. 109:170-179 (2007)).*
Thurber et al. (Adv. Drug Deliv. Rev. 60:1421-1434 (2008)).*
Rudnick et al. (Can. Biotherp. & Radiopharm. 24: 155-162 (2009)).*
Lallatin, U.S. Appl. No. 12/328,379 (not yet published as PGPub).*
U.S. Appl. No. 60/567,344, filed Apr. 30, 2004, Lallatin.
Balzarini et al. (1982) "Role of Thymidine Kinase in the Inhibitory Activity of 5-Substituted-2'Deoxyuridines on the Growth of Human and Murine Tumor Cell Lines," Biochem. Pharmacol. 31(6):1089-1095.
Baron et al. (1990) "A Rapid Two-Step Purification of Rat Liver Fetal Thymidine Kinase," Preparative Biochem. 20 (3-4):241-256.
Boivin et al. (2002) "Intranasal Herpes Simplex Virus Type 2 Inoculation Causes a Profound Thymidine Kinase Dependent Cerebral Inflammatory Response in the Mouse Hindbrain," Eur. J. Neurosci. 16(1):29-43.
Bradshaw, H.D. Jr. (1983) "Molecular Cloning and Cell-Specific Regulation of a Functional Human Thymidine Kinase Gene," Proc. Natl. Acad. Sci. USA 80:5588-5591.
Bronzert et al. (1981) "Purification and Properties of the Estrogen-Responsive Cytoplasmic Thymidine Kinase from Human Breast Cancer," Cancer Res. 41:604-610.
Daugherty et al. (1991) "Polymerase Chain Reaction Facilitates the Cloning, CDR-Grafting, and Rapid Expression of a Murine Monoclonal Antibody Directed Against the CD18 Component of Leukocyte Integrins," Nuc. Acids Res. 19 (9):2471-2476.
Ellims et al. (1982) "Human Thymidine Kinase: Purification and Some Properties of the TK1 Isoenzyme from Placenta," Mol. Cell. Biochem. 45:113-116.
Flemington (1987) "Sequence, Structure and Promoter Characterization of the Human Thymidine Gene," Gene 52:267-277.
Gan et al. (1983) "Human Thymidine Kinase," J. Biol. Chem. 258:7000-7004.
Goding et al. (1980) "Antibody Production by Hybridomas," J. Immunol. Methods 39:285-308.
Gronowitz et al. (1984) "Application of an In Vitro Assay for Serum Thymidine Kinase: Results on Viral Disease and Malignancies in Humans," Int. J. Cancer 33:5-12.

(Continued)

*Primary Examiner*—Lynn Bristol
(74) *Attorney, Agent, or Firm*—e winner & associates, pllc

(57) ABSTRACT

Monoclonal antibodies to thymidine kinase 1 are disclosed which are useful in methods of detecting, diagnosing, and treating cancer.

11 Claims, 14 Drawing Sheets

OTHER PUBLICATIONS

Habteyesus et al. (1991) "Deoxynucleside Phosphorylating Enzymes in Monkey and Human Tissues Show Great Similarities, While Mouse Deoxycytidine Kinase has a Different Substrate Specificity," Biochem. Pharmacol. 42(9): P1829-P1836.

Hannigan et al. (1993) "Thymidine Kinase: The Enzymes and Their Clinical Usefulness," Cancer Biother. 8 (3):187-197.

Hengstschlager et al. (1994) "Different Regulation of Thymidine Kinase During the Cell Cycle of Normal Versus DNA Tumor Virus-Transformed Cells," J. Biol. Chem. 269:13836-13842.

Hengstschlager et al. (1994) "A Common Regulation of Genes Encoding Enzymes of the Deoxynucleotide Metabolism is Lost After Neoplastic Transformation," Cell Growth Differ. 5(12):1389-1394.

Hengstschlager et al. (1993) "Cytofluorometric Assay for the Determination of Thymidine Uptake and Phosphorylation in Living Cells," Cytometry 14:39-445.

Jansson et al. (1992) "Mammalian Thymidine Kinase 2, Direct Photoaffinity Labeling with [32P]dTTP of the Enzyme from Spleen, Liver, Heart and Brain," Eur. J. Biochem. 206(2):485-490.

Kohler et al. (1976) "Derivation of Specific Antibody-Producing Tissue Culture and Tumor Lines by Cell Fusion," Eur. J. Immunol. 6:511-519.

Lau et al. (1994) "Direct Isolation of the Functional Human Thymidine Kinase Gene W/A Cosmid Shuttle Vector," Proc. Natl. Acad. Sci. USA 81:414-418.

May et al. (1991) "Intracellular Routing Rather than Cross-Linking or Rate of Internalization Determines the Potency of Immunotoxins Directed Against Different Epitopes of sIgD on Murine B Cells," Cell Immunol. 135:490-500.

McKenna et al. (1988) "Thymidine Kinase Activities in Mononuclear Leucocytes and Serum from Breast Cancer Patients," Br. J. Cancer 57:619-622.

Munch-Peterson et al. (1990) "Thymidine Kinase in Human Leukemia—Expression of Three Isoenzyme Variants in Six Patients with Chronic Myelocytic Leukemia," Leuk. Res. 14:39-45.

Munch-Peterson et al. (1991) "Diverging Substrate Specificity of Pure Human Thymidine Kinases 1 and 2 Against antiviral Dideoxynucleosides," J. Biol. Chem. 266:9032-9038.

Munch Peterson et al. (1993) "Reversible ATP-Dependent Transition Between Two Forms of Human Cytosolic Thymidine Kinase With Different Enzymatic Properties," J. Biol. Chem. 268(21):15621-15625.

Oldham et al. (1993) "Whats the Score," Cancer Biother. 8(3):187-188.

O'Neill et al. (1992) "Can Thymidine Kinase Levels in Breast Tumors Predict Disease Recurrence," J. Nat. Cancer Inst. 84(23):1825-1828.

O'Neill et al. (1987) "Elevated Serum and Mononuclear Leukocyte Thymidine Kinase Activities in Patients with Cancer," Irish Med. J. 80(9):264-265.

Seaver et al. (1994) "Monoclonal Antibodies in Industry: More Difficult Than Originally Thought," Genetic Eng. News pp. 10,21.

Sherley et al. (1988) "Human Cytosolic Thymidine Kinase," J. Biol. Chem. 263:375-391.

Tamiya et al. (1989) "Co-Purification of Thymidylate Kinase and Cytosolic Thymidine Kinase from Human Term Placenta by Affinity Chromatography," Biochem. Biophys. Acta 995:28-35.

Topolcan et al. (2005) "Changes of Thymidine Kinase (TK) During Adjuvant and Palliative Chemotherapy," Anticancer Res. 25:1831-1834.

Willingham et al. (1987) "*Pseudomonas* Exotoxin Coupled to a Monoclonal Antibody Against Ovarian Cancer Inhibits the Growth of Human Ovarian Cancer Cells in a Mouse Model," Proc. Natl. Acad. Sci. USA 84:2474-2478.

He, Q. et al. "The clinical significance of thymidine kinase 1 measurement in serum of breast cancer patients using anti-TK1 anitbody," *The International Journal of Biological Markers*, Apr.-Jun. 2000, vol. 15, No. 2, pp. 139-146.

Nesterova, M. et al. "Autoantibody biomarker opens a new gateway for cancer diagnosis," *Biochimica et Biophysica Acta* 1762 (2006) 398-403.

Wu, Chuanjing et al. "Production and characterization of a novel chicken IgY antibody raised against C-terminal peptide from human thymidine kinase 1," *Journal of Immunological Methods*, Jun. 1, 2003, vol. 277, No. 1-2, pp. 157-169.

Yagihashi, Atsuhito et al. "Detection of autoantibodies to survivin and livin in sera from patients with breast cancer," *Clinica Chimica Acta* 362 (2005) 125-130.

Zhang, Jian-Ying et al. "Enhancement of Antibody Detection in Cancer Using Panel of Recombinant Tumor-associated Antigens," *Cancer Epidemiology, Biomarkers & Prevention*, 2003, vol. 12, 136-143.

Carter et al. (1992) "Humanization of an anti-p185$^{HER2}$ antibody for human cancer therapy," *Proc. Natl. Acad. Sci. USA*, 89:4285-4289.

Co et al. (1994) "A Humanized Antibody Specific for the Platelet Integrin gpIIb/IIIa," *Journal of Immunology*, 152: 2968-2976.

Robinson et al. (2004) "Improving Monoclonal Antibodies for Cancer Therapy," *Drug Development Research*, 61:172-187.

Barrett, J.T. (1983), "Textbook of Immunology," p. 249.

Cruse et al. (2004), "Atlas of Immunology," Second Edition, CRC Press, pp. 282 and 640.

Kauffman et al. (1991), "Cell cycle regulation of thymidine kinase: Residues near the carboxyl terminus are essential for the specific degradation of the enzyme at mitosis," *Mol. Cell Biol*. 11:2538-2446.

Stites et al. (1991), "Basic and Clinical Immunology," Seventh Edition, p. 584.

* cited by examiner

ANTI-CANCER ACTIVITY OF AN ANTI-THYMIDINE KINASE MONOCLONAL ANTIBODY

RELATED APPLICATIONS

This application claims priority to U.S. Provisional Application No. 60/573,429, filed May 21, 2004 which is incorporated herein by reference in its entirety.

BACKGROUND OF THE INVENTION

1. Field of the Invention

Embodiments of the invention relate to treatment of cancer with a monoclonal antibody to an S-phase regulated specific protein, particularly thymidine kinase.

2. Description of the Related Art

The S-phase is the portion of the cell cycle during which DNA replication takes place. Expression of genes related to DNA replication is maximal during early S-phase.

TK-1 is a cellular enzyme which is involved in a "salvage pathway" of DNA synthesis. In normal growing cells thymidine kinase 1 mRNA rises near the G1-S boundary, peaks in early S phase, and returns in G2 to approximately the level of early G1. It is activated in the G1/S phase of the cell cycle, and its activity has been shown to correlate with the proliferative activity of tumor cells. Malignant cells appear to have lost the strict regulation of TK1 that is observed in normal cells. TK activity is a major biochemical marker of cell proliferation and several studies show that TK levels are elevated in malignancies. The elevated TK activity is due to an increase in the TK1 isozyme. The elevation of TK1 levels in malignancies is not simply the result of cellular proliferation but is directly caused by alteration of regulatory mechanisms in cancer cells, which constitutively express TK1 mRNA.

The use of MAb to specifically target malignant cells is an approach which can leave normal or uninfected tissue or cells unharmed. MAbs may be used to construct therapeutic reagents with selectivity for certain populations of cells. Optionally, MAbs or other cell targeting proteins are linked to bioactive moieties to form biotherapeutic agents referred to as immunoconjugates, immunotoxins or fusion proteins, which can combine the selectivity of the targeting moiety with the potency of the bioactive moiety. Embodiments of the invention are directed to the use of anti-TK1 antibody to inhibit cell proliferation in cells that synthesize and overexpress TK1 such as cancer cells.

U.S. Pat. No. 5,698,409, which is incorporated herein by reference, describes a purified mammalian thymidine kinase 1 (TK1) from Raji cells and a TK1 monoclonal antibody. The monoclonal antibody binds to TK1 and inhibits TK1 activity. The TK1 monoclonal antibody was used for cancer diagnosis.

SUMMARY OF THE INVENTION

Preferred embodiments of the invention are directed to a method for treating cancer in a mammal, by administering to said mammal an amount of a pharmaceutical composition which includes an antibody to an S-phase regulated protein or a fragment thereof, sufficient to inhibit cell proliferation in the mammal. In preferred embodiments, the antibody is an anti-TK1 monoclonal antibody. More preferably, the anti-TK1 monoclonal antibody is CB001 (a hybridoma cell line producing this antibody was deposited with the American Type Culture Collection (ATCC), 10801 University Blvd, Manassas, Va. 20110-2209, as Deposit No. PTA-6704 on May 5, 2005). In preferred embodiments, the anti-TK1 antibody is a chimeric, humanized, or fully human monoclonal antibody.

In some preferred embodiments, the pharmaceutical composition also includes a second anti-cancer agent. Preferably, the second anti-cancer agent is a nucleoside analog. More preferably, the nucleoside analog is 5' fluorouracil, fludarabine, cladribine, cytarabine, gemcitabine, capecitabine, troxacitabine, zidovudine/lamnivudine (Combivir®), emtricitabine (Emtriva®), emtricitabine (Epivir®), zalcitabine (Hivid®) zidovudine (Retrovir®), abacavir/zidovudine/lamivudine (Trizivir®), didanosine (Videx®, VidexEC®), tenofovir disoproxil fumarate (Viread®), stavudine (Zerit®), or abacavir (Ziagen®).

In some preferred embodiments, the anti-TK1 antibody is conjugated to a cytotoxic agent. More preferably, the cytotoxic agent is pokeweed antiviral protein (PAP), ricin, abrin, gelonin, saporin, or alpha-sarcin.

In some preferred embodiments, prior to administering the pharmaceutical composition, the mammal is treated with sufficient radiation to up-regulate TK1 expression.

In preferred embodiments, the pharmaceutical composition also includes a pharmaceutically acceptable liquid carrier adapted for parenteral administration. Preferably, the liquid carrier includes isotonic saline.

Preferred embodiments of the invention are directed to a method for diagnosing cancer in a mammal, including the steps of:
- obtaining a sample from the mammal;
- incubating the sample with an anti-TK1 antibody or fragment thereof;
- detecting an amount of antibody-TK1 complex;
- quantifying the concentration of TK1 in the sample by comparing the detected amount of antibody-TK1 complex with a standard curve generated using known amounts of TK1; and
- diagnosing the presence of cancer in the mammal based on the concentration of TK1 in the sample.

Preferred embodiments of the invention are directed to a monoclonal antibody to TK1. Preferably, the TK1 is a viral or mammalian TK1. More preferably, the TK1 is a human TK1. In some preferred embodiments, the antibody is specific to an active TK1. In alternate preferred embodiments, the antibody is specific to an inactive TK1. In some preferred embodiments, the antibody is specific to a multimeric form of TK1. In alternate preferred embodiments, the antibody is specific to a monomeric form of TK1. In some preferred embodiments, the monoclonal antibody does not react with a 100 kD subunit of TK1. In some preferred embodiments, the monoclonal antibody is capable of binding to TK1, but does not affect the enzymatic activity of TK1. In preferred embodiments, the monoclonal antibody is a chimeric, humanized, or fully human monoclonal antibody.

Preferred embodiments of the invention are directed to a method of making a monoclonal antibody against TK1 including the step of chemically synthesizing TK1 or a fragment thereof for use as an antigen. Preferably, the chemically synthesized TK1 includes at least a part of the known TK1 protein sequence.

Preferred embodiments of the invention are directed to a method of making a monoclonal antibody against TK1 including the step of expressing at least a part of a gene encoding TK1 in a host cell.

Preferred embodiments of the invention are directed to a method of determining location and spread of neoplastic tissue in a patient including the steps of:
- administering a labeled TK1 antibody to a patient;

visualizing the labeled TK1 antibody; and
determining the location and extent of spread of neoplastic tissue in the patient.

Preferably, the visualization is by PET, MRI, CT, or SPECT. Preferably, the TK1 antibody is labeled with a radioactive or radio-opaque dye. In preferred embodiments, determining the location and extent of spread of neoplastic tissue in the patient is used in a surgical procedure to allow the physician to visually differentiate neoplastic tissue from normal tissue.

Further aspects, features and advantages of this invention will become apparent from the detailed description of the preferred embodiments which follow.

BRIEF DESCRIPTION OF THE DRAWINGS

These and other feature of this invention will now be described with reference to the drawings of preferred embodiments which are intended to illustrate and not to limit the invention.

DETAILED DESCRIPTION OF THE PREFERRED EMBODIMENT

Figure 1:
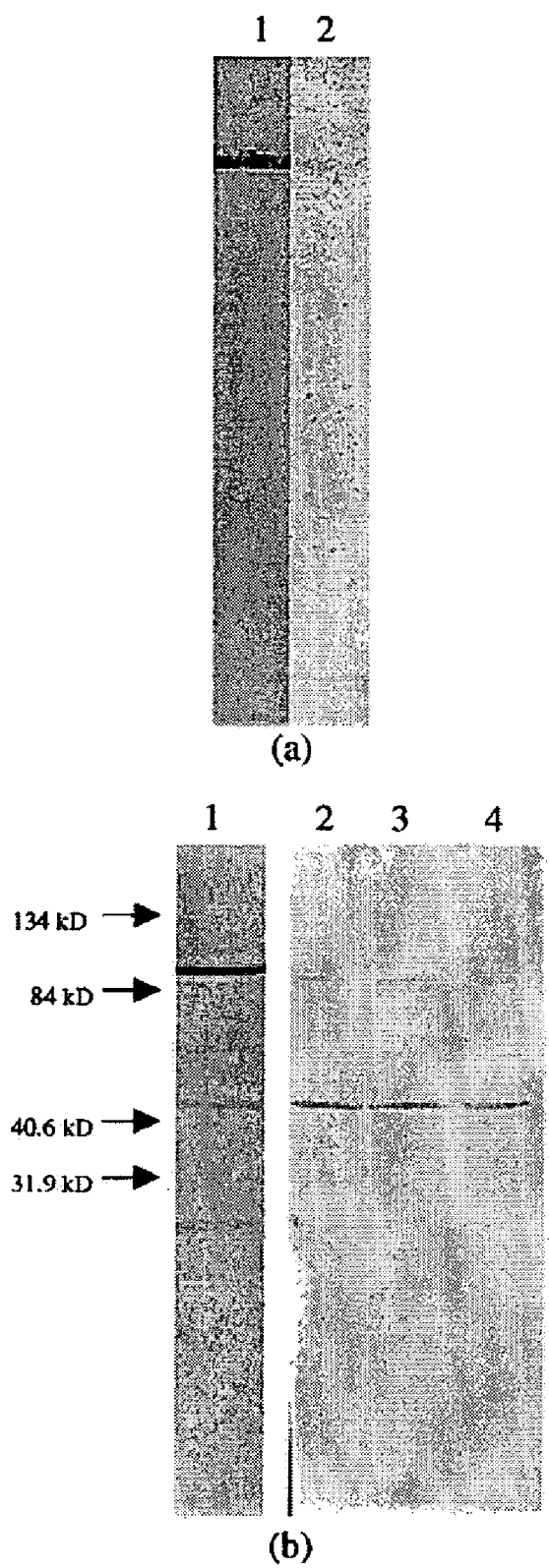
FIG. 1 shows a Western blot assay showing TK1 specificity of clone 14F2. Samples were separated using a native or a partial denature 12% polyacrylamide gel (using methods similar to the production of the MAb), as described in the Materials and Methods Section. Polypeptides were then transferred onto a nitrocellulose filter and probed with MAb from clone 14F2. A conjugate antibody solution containing goat anti-mouse IgG (H1L chains) horseradish peroxidase was used to visualize MAb binding. (a) Lane 1, purified TK1, native sample, Ponceau S staining; Lane 2, purified TK1, native sample, Western blot. (b) Lane 1, purified TK1, partial denature sample, Ponceau S staining; Lane 2, Purified TK1, partial denature sample, Western blot; Lane 3, Raji cell extract, partial denature sample, Western blot; Lane 4, Hela cell extract, partial denature sample, Western blot.
Figure 2:
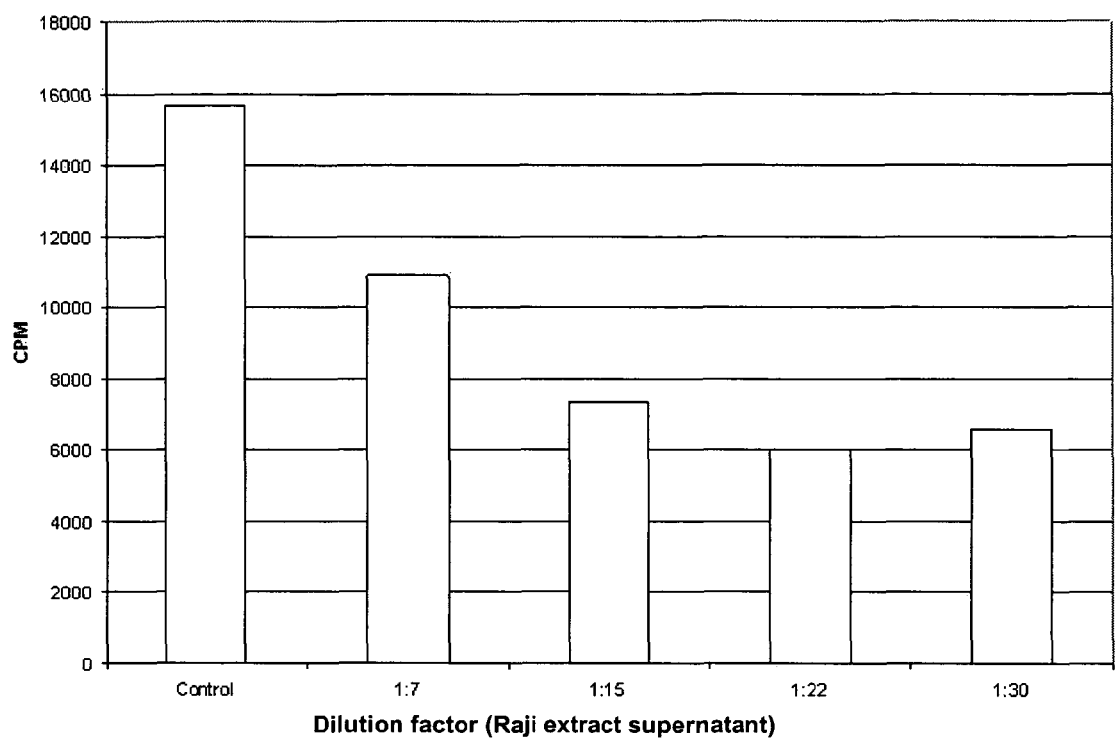
FIG. 2 shows the effect of CB001 MAb to TK1 on TK1 enzyme activity.
Figure 3:
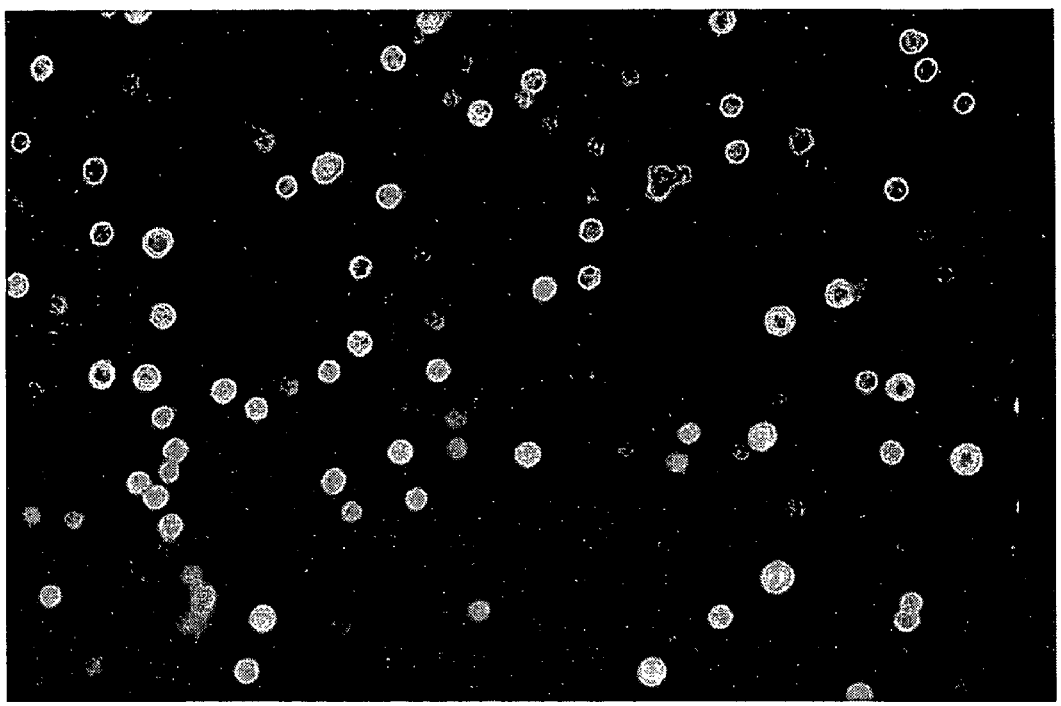
FIG. 3 shows Raji cells stained with CB001 Ab at 100× magnification.
Figure 4:
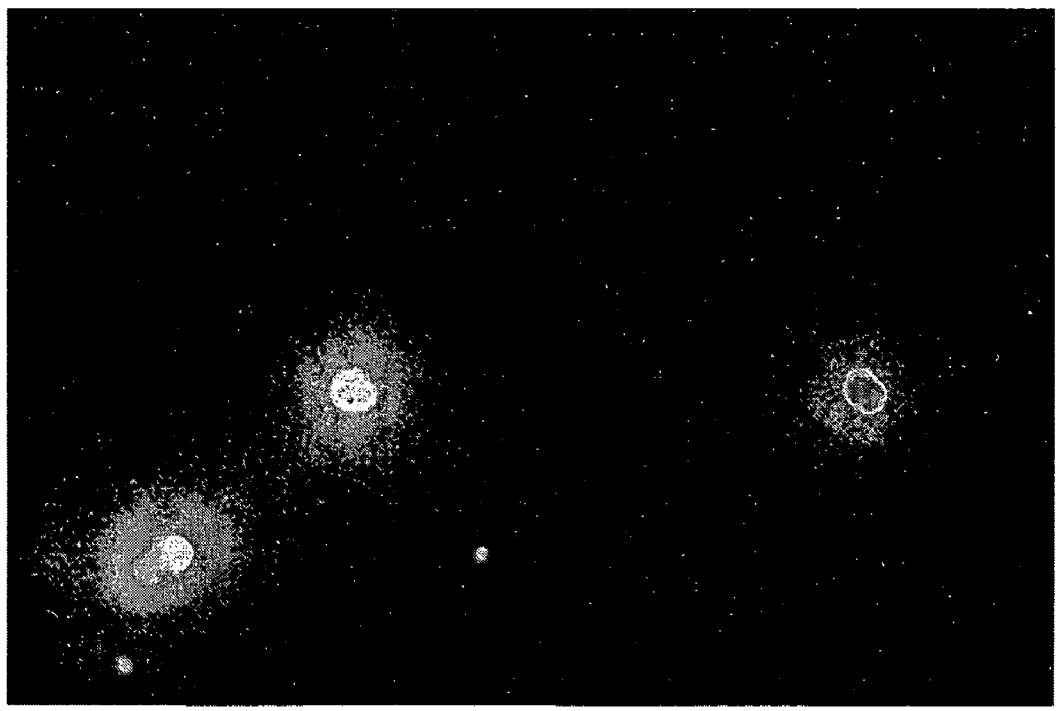
FIG. 4 shows Raji cells stained with CB001 Ab at 500× magnification.
Figure 5:
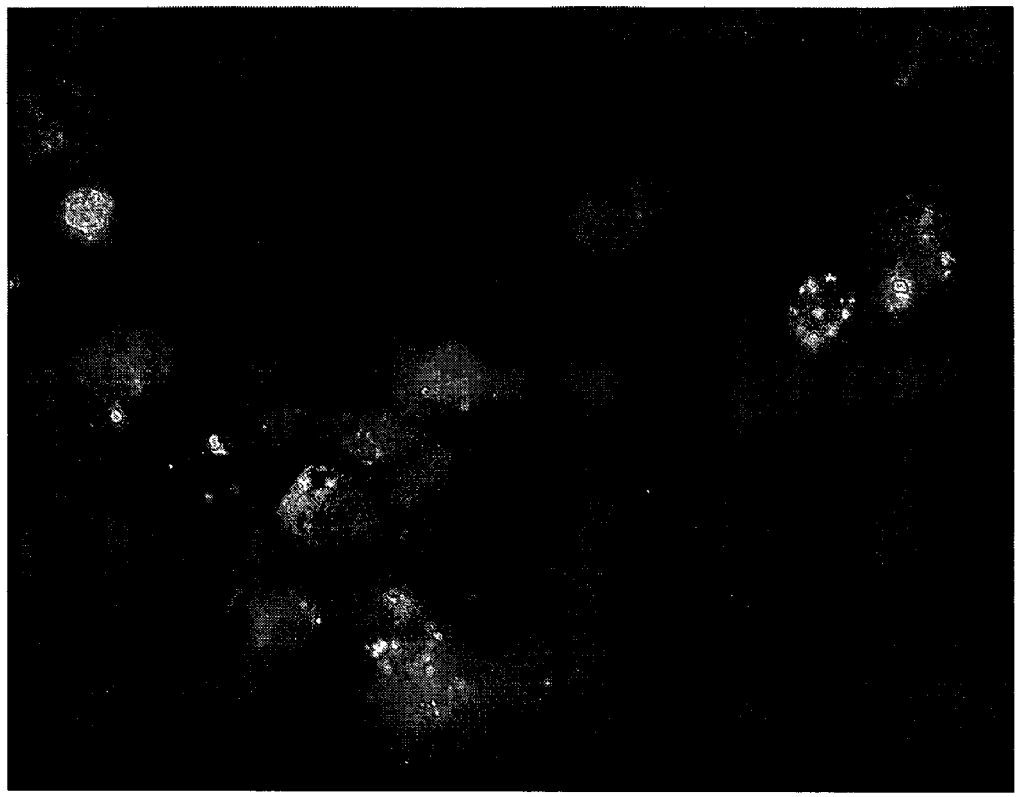
FIG. 5 shows MD-MBA-231 cells stained with CB001 Ab at 400× magnification.
Figure 6:
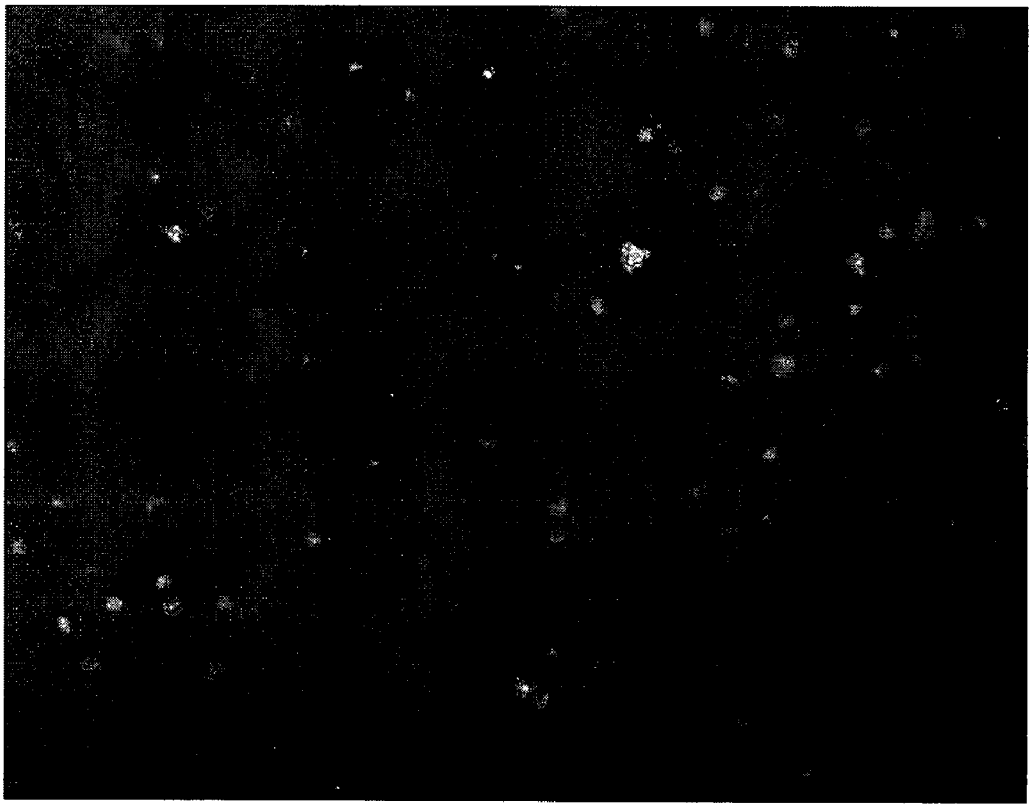
FIG. 6 shows MD-MBA-231 cells stained with CB001 Ab at 100× magnification.
Figure 7:
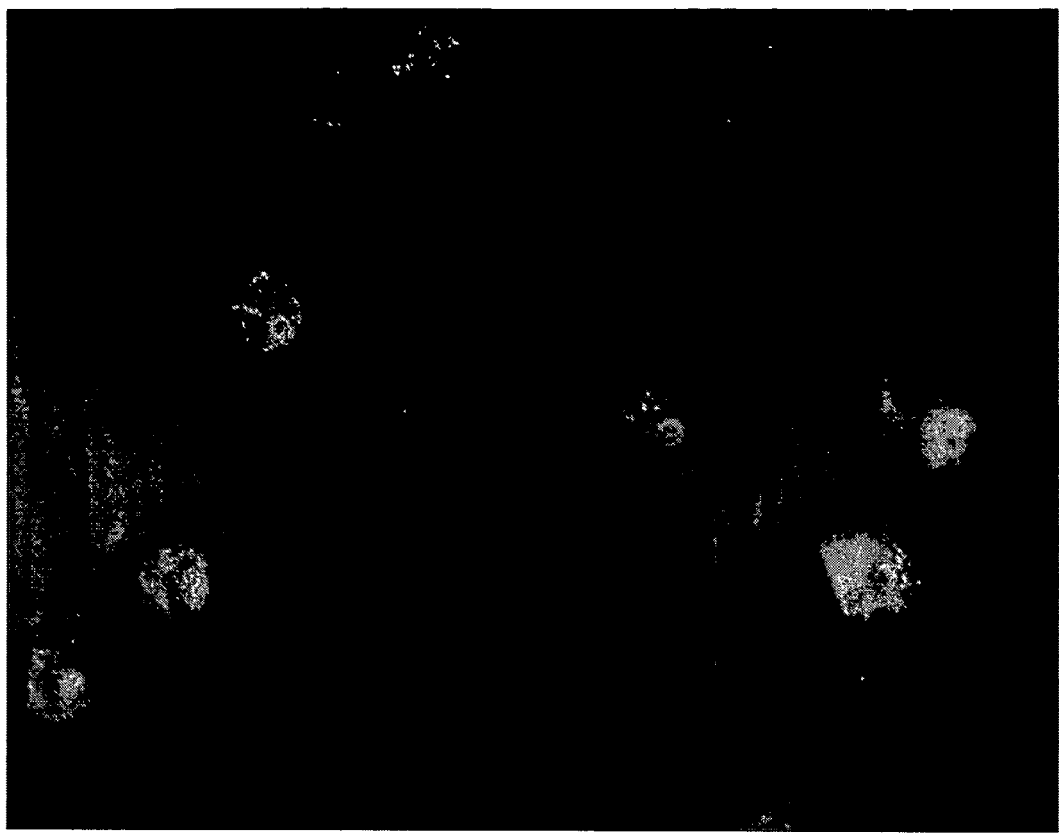
FIG. 7 shows MD-MBA-435 cells stained with CB001 Ab at 400× magnification.
Figure 8:
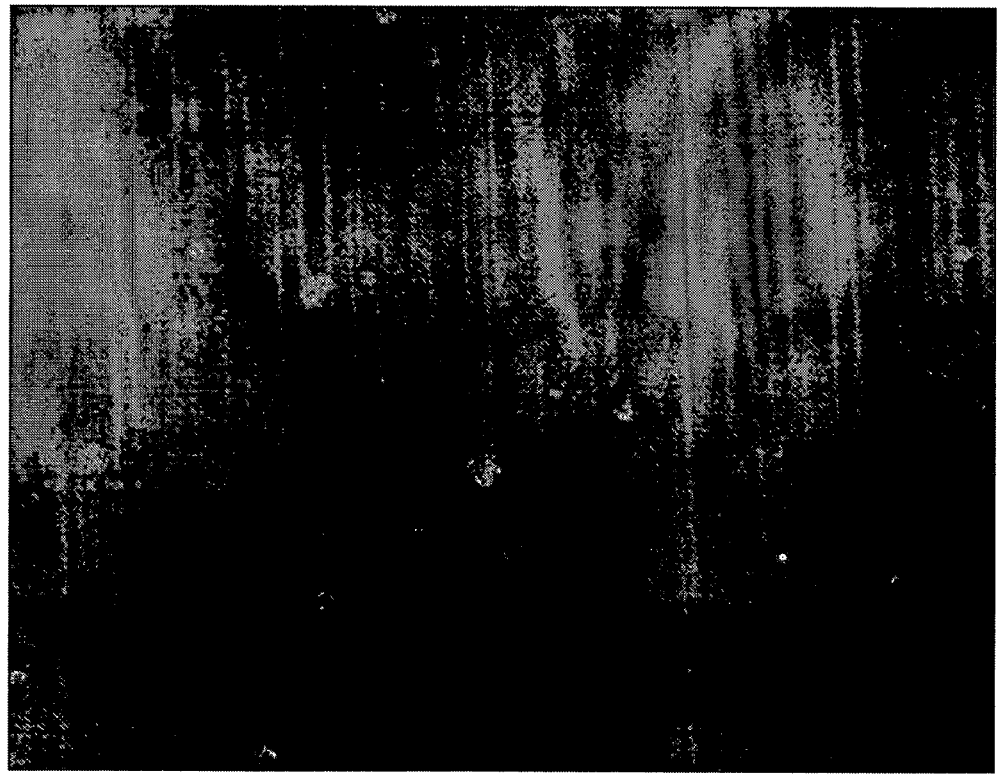
FIG. 8 shows PANC-1 (pancreatic) cells stained with CB001 antibody at 100× magnification.
Figure 9:
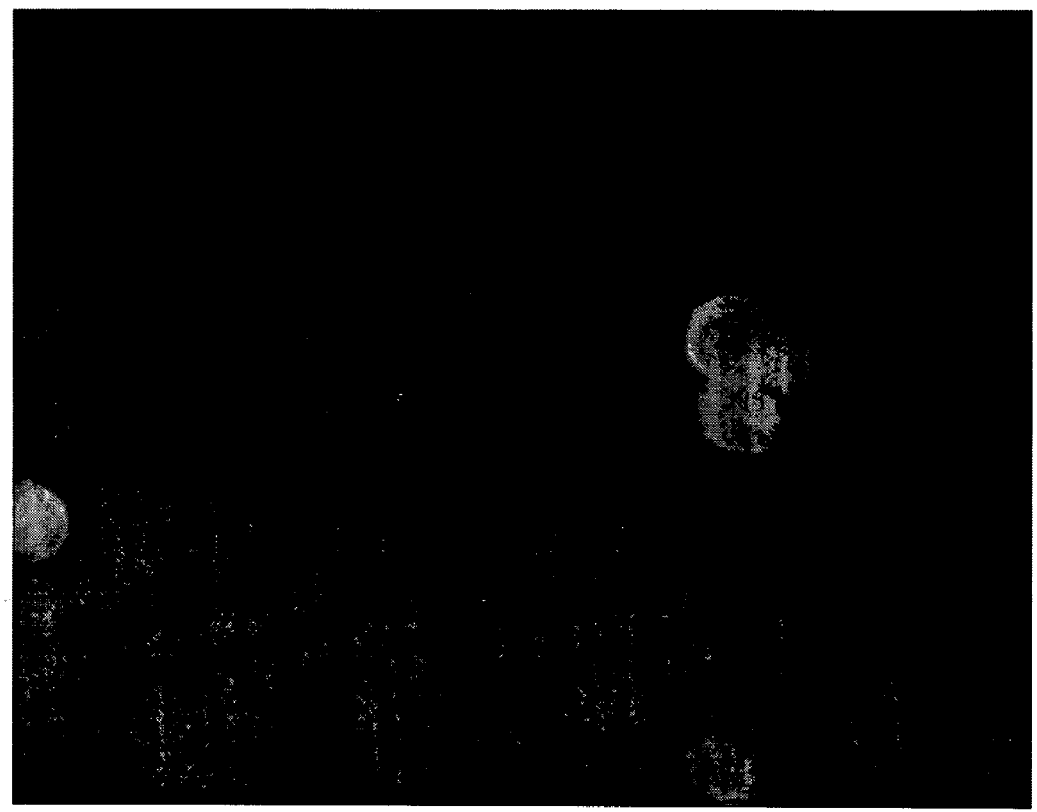
FIG. 9 shows PANC-1 (pancreatic) cells stained with CB001 antibody at 400× magnification.
Figure 10:
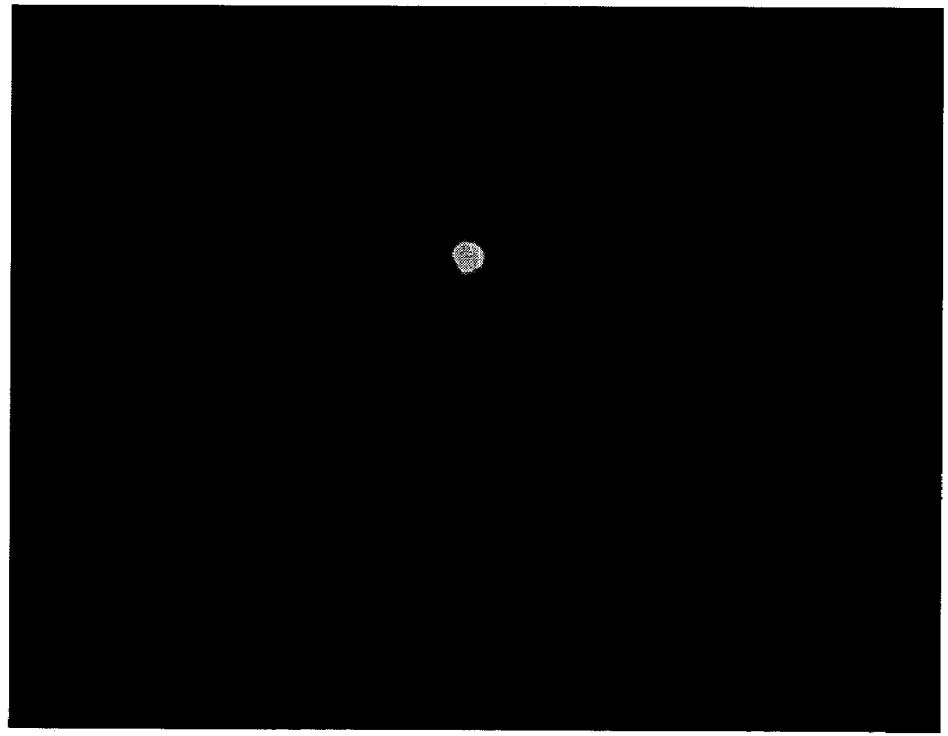
FIG. 10 shows Hep-G2 (hepatocytic) cells stained with CB001 antibody at 400× magnification (far fewer cells in the field).
Figure 11:
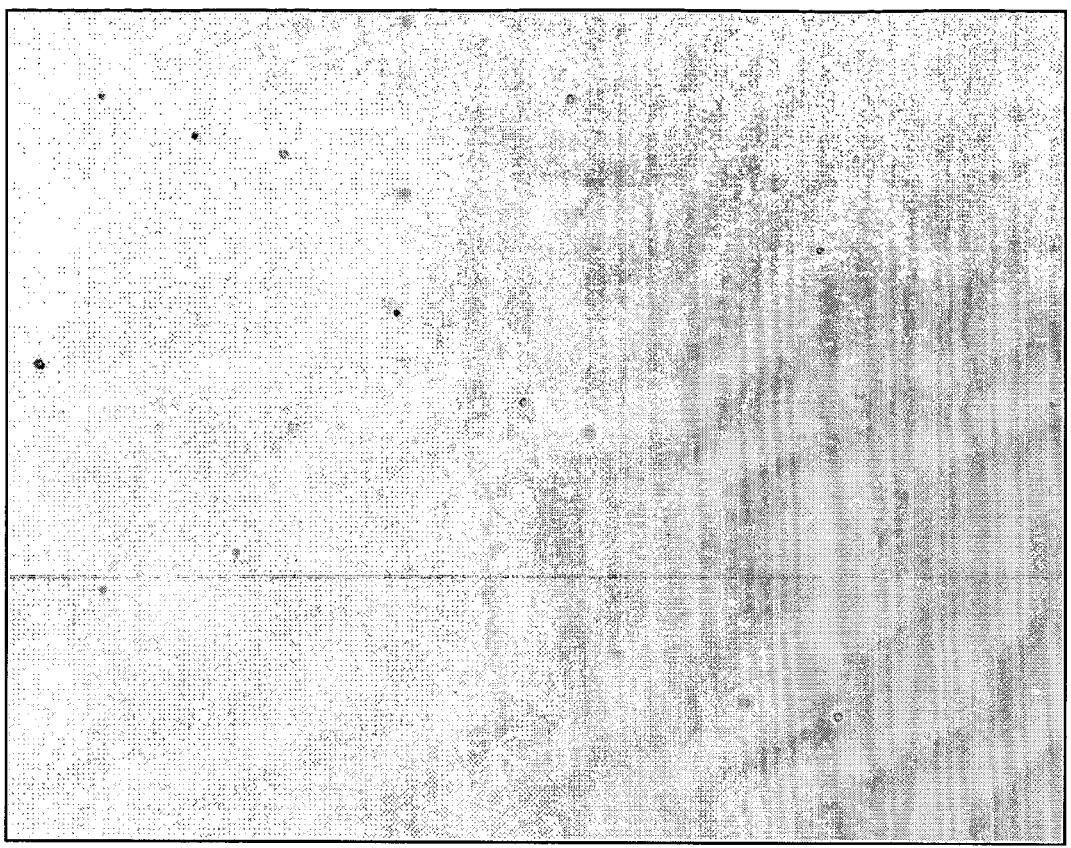
FIG. 11 shows normal human lymphocytes stained with CB001 antibody using light microscopy at 100×.
Figure 12:
FIG. 12 shows normal human lymphocytes stained with CB001 antibody using fluorescence microscopy at 100×.

While the described embodiment represents the preferred embodiment of the present invention, it is to be understood that modifications will occur to those skilled in the art without departing from the spirit of the invention. The scope of the invention is therefore to be determined solely by the appended claims.

The following definitions are provided in order to provide clarity as to the intent or scope of their usage in the specification and claims.

The term "purified thymidine kinase 1" or "TK1" as used herein refers to TK1 isolated from any organism but particularly a mammal, including, but not limited to, a mammalian body organ, tissue, cell, fluid and the like, in either normal or diseased condition, and presented as a fresh or preserved specimen, a cell tissue culture, a cell line, a hybridoma, etc. TK 1 prepared from a virus or virally-infected cell is also specifically included in the term "TK1." TK1 can also be prepared by recombinant methods in an appropriate host cell or may be chemically synthesized. TK1 sequences are known and available including sequence information for human TK1. The purified TK1 of the invention provides a yield of purified TK1 sufficient for the preparation of monoclonal antibodies.

The term "mammalian" as used herein refers to a human or other animal classified as a mammal.

The term mammalian "body sample" as used herein refers to a sample from a mammal, including, but not limited to, a body organ, tissue, cell, fluid, etc., in either normal or diseased condition and presented as a fresh or preserved specimen.

The term "body fluid" as used herein refers to any fluid obtained from a mammal, for example, blood, serum, urine, spinal fluid, tears, etc.

The term "body tissue" as used herein refers to any normal or diseased tissue obtained from a mammal, for example, organ tissue, biopsy tissue, tumors, etc. A body tissue may be presented as a fresh or preserved (e.g., frozen) sample, a histological slide preparation, etc.

The terms "antibody" or "immunoglobulin" are used generally to include polyclonal and monoclonal antibodies, and fragments thereof which exhibit the desired binding specificity and affinity, regardless of the source or immunoglobulin type (i.e., IgG, IgE, IgM, etc.). The term "antibody to TK1", "TK1 antibody" or "anti-TK1 antibody" as used herein refers to an antibody or fragment thereof that binds to TK1. The term "monoclonal antibody" is used in accordance with its ordinary meaning to denote a homogenous immunoglobulin resulting from the proliferation of a single clone of cells (e.g., hybridoma cells, eukaryotic host cells transfected with DNA encoding the homogenous immunoglobulin, prokaryotic host cells transformed with DNA encoding the homogenous immunoglobulin, etc.), and which is generally characterized by heavy chains of a single class and subclass, and light chains of a single type. It is contemplated that in some applications a polyclonal antibody to a purified TK1 of the instant invention can be utilized in place of an anti-TK1 monoclonal antibody of the invention. Note that not all TK1 antibodies inhibit the TK1 enzymatic activity because not all epitopes are at the catalytic site. Some antibodies were obtained that bound to TK1 but did not inhibit the TK1 enzymatic activity.

The term "therapeutic application" as used herein refers to any use of TK1, monoclonal anti-TK1 antibodies, or polyclonal anti-TK1 antibodies to target diseased tissues, wherein said diseased tissues proliferation is targeted, visualized, decreased or eliminated. It is contemplated that the therapeutic applications of this invention may be used in conjunction with or in isolation from other now known or yet to be discovered therapeutic applications.

The term "therapeutic or biotherapeutic agent" is used in its ordinary sense and to include the use of a MAb, pharmaceutical, protein or peptide, nucleic acid, etc. to treat or prevent disease or other abnormality in a mammal such as a human.

The term "complement mediated lysis" as used herein refers to a system of serum proteins activated by antibody-antigen complexes, which helps eliminate selected cells by directly causing their lysis or by promoting their phagocytosis.

The terms "chimeric", "humanized immunoglobulin" or "humanized antibody" are used in their ordinary meanings and include any immunoglobulin or antibody or fragment thereof, produced at least partly in a non-human mammal, wherein at least one portion is of human origin.

S-phase proteins involved in cell proliferation, that is, cyclins, oncoproteins, growth factors, proteins involved in signal transduction and DNA repair and/or synthesis proteins provide potential targets for cancer therapy using MAb's to the targeted protein. Potential targets include S phase regulated proteins such as thymidine kinase 1 (TK1), deoxycytidine kinase, thymidylate kinase (TmpK), adenylate kinase (AmpK), uridine monophosphate/cytidine monophosphate kinase (Ump/CmpK), guanylate kinase (GmpK), Nucleoside diphosphate kinase (NDK), Epstein Barr thymidine kinase, and herpes simplex virus type 1 thymidine kinase (HSV1-TK). Monoclonal antibodies to S-phase regulated proteins are used to provide a cancer treatment. S-phase proteins such as TK1 are found on the surface of proliferating cells such as cancer cells. MAbs to TK1 will preferentially bind to cancer cells as normal cells do not express TK1. Once the anti-TK1 MAb has bound to the cancer cell, the cells are susceptible to destruction by ADCC and CDC. Alternatively, the cancer cell may be killed by an immunotoxin attached to the anti-TK1 antibody. Thus, administration of a biotherapeutic agent containing MAbs to one or more S-phase regulated proteins arrests cell proliferation and is useful as a cancer treatment. The MAbs described may be used in combination with a second agent such as an immunotoxin or a second therapeutic for treatment of cancer. In a preferred embodiment, the S-phase regulated protein is TK1.

The following described embodiments for the production of anti-TK1 are to be considered in all respects only as illustrative and not restrictive. In preferred embodiments, the current invention contemplates the production of various antibodies comprising antibodies specific to active TK1, inactive TK1, synthetic peptides derived from components of the TK1 gene, multimeric TK1, and monomeric TK1. Additionally, in preferred embodiments, the current invention contemplates the production of various anti-TK1 antibodies, which are specific to various TK1 epitopes. Consequently, the scope of this disclosure should not be read as to limit the invention to a finite number of antibodies or to a finite number of epitopes on TK1.

Surprisingly, the present inventors have found that TK1 is found on the surface of proliferating cells such as cancerous cells and viral-infected cells, but not normal cells. The expression of TK1 on the surface of cancerous and viral-infected cells makes them susceptible to ADCC and CDC. TK1 expression is increased 6-30 times in cancer cells and during viral transformation or infection of mammalian cells. These observations are utilized in methods disclosed herein for treating cancer cells with an antibody to thymidine kinase. Methods based upon the observed mechanism pertaining to the treatment of virally-infected cells are disclosed in U.S. provisional application No. 60/567,344, filed Apr. 30, 2004, which is incorporated herein by reference.

It has been demonstrated that TK1 mRNA and protein are up-regulated and constitutively expressed in transformed cells such as cancer cells. TK1 levels are not detectable in quiescent cells. Cancer cells are selectively targeted and killed via complement dependent lysis (CDC) or antibody dependent cellular cytotoxicity (ADCC) by treating patients with anti-TK1 antibody according to preferred embodiments of the invention.

In some embodiments, the cytotoxicity of TK1 antibody is enhanced by first treating patients with radiation therapy, which has been shown to up-regulate TK1 expression (because the DNA damage requires the generation of new nucleotides for DNA repair). After up-regulation of TK1 expression, the patient is treated with the TK1 antibody which binds the TK1 on the cell surface. By focusing the radiation therapy we can limit the toxicity—if any—of the antibody to the site of the tumor.

Additionally, this invention contemplates using anti-TK1 antibodies which may be useful for targeted therapy. For example, the anti-TK1 antibody is used to inhibit the elevated levels of TK1 and to restore a normal level of TK1, which helps reduce cellular replication. The anti-TK1 antibody may be used to inhibit the elevated level and to restore a normal level of TK1 enzyme activity in the tumor cells, which may decrease cellular proliferation and halt spread of the disease.

An example of this embodiment comprises the use of anti-TK1 monoclonal antibodies used as a therapeutic agent, which can bind TK1 in cancer patients and reduce proliferation. Because TK1 is a salvage pathway enzyme, treatment with anti-TK1 monoclonal antibody should have minor effects on normal tissue and allow all cells that proliferate by the normal pathway to divide normally and leave non-proliferating cells unharmed. The biosynthesis of dTTP via Thymidine kinase (TK) is not essential for DNA synthesis. The de novo synthesis of dTMP is achieved through a complex series of reactions in which aspartate and carbamoyl-phosphate are the starting blocks for the biosynthesis of dUDP, which is converted to dTMP by thymidylate synthatase. Dividing cells require a significant intracellular pool of dTTP for cell survival. The de novo synthesis of dTTP is expensive to the cell in terms of available resources. The direct conversion of Thymidine to dTMP by TK circumvents the de novo pathway. This recycling of nucleotides has been termed the "salvage pathway."

Embodiments of the present invention provide a biotherapeutic agent which is a monoclonal antibody to TK1. In some embodiments, the biotherapeutic agent is an immunoconjugate or immunotoxin, which includes a monoclonal antibody specific to TK1, linked to an effective amount of a moiety, e.g., a polypeptide or a toxin, which has biological activity. Examples of useful biologically active moieties include ricin A chain immunotoxin, saporin, gelonin, *Pseudomonas* exotoxin or Pokeweed antiviral protein or an active fragment thereof. The activity of a preparation of pokeweed antiviral protein can be determined by methods which are described in U.S. Pat. No. 6,372,217 which is incorporated herein by reference. However, it is emphasized that it is not necessary to conjugate TK1 to an immunotoxin. The use of monoclonal antibody to TK1 alone specifically kills cancer cells by activation of complement-mediated lysis.

It is preferred that the anti-TK1 biotherapeutic agent of the present invention employs the monoclonal antibody TK1 or a biologically active subunit, fragment or derivative thereof, which binds to TK1 present at the surface of actively proliferating cells such as cancer cells. A "biologically active" subunit or fragment of a monoclonal antibody has at least about 1%, preferably at least about 10%, and more preferably at least about 50%, of the binding activity of the monoclonal antibody. These biotherapeutic agents are active both in vitro and in vivo, and are useful to treat diseases, such as certain cancers. As used herein, the term monoclonal antibody (MAb) includes fragments, subunits and derivatives thereof. Preferably, the MAb is an anti-TK1 MAb.

The present invention provides a method to treat cancer or inhibit proliferation of cancer cells in mammals. The method comprises treating a mammal such as a human or mammalian cells in vitro or in vivo with an effective amount of either an antibody to TK1 or an immunoconjugate which includes an antibody to TK1.

In some embodiments, the patient is first treated with a MAb to TK that is immunologically inactive. This MAb binds to TK on cancer cells and would also bind TK1 on normal cells should any express TK1. Next the patient is treated with an immunologically active anti-TK1 antibody to specifically bind to TK1 only on the surface of cancer cells because of the anticipated contrast in the high level of TK1 expression between cancer cells and the low or non-existent level of TK1 expression in normal, or dividing cells. The cancer cells are then killed by CDC or ADCC. It is emphasized that this method is only necessary if there is some cross-reactivity of the anti-TK1 antibody with normal cells.

In some embodiments, the anti-TK1 biotherapeutic agent is used in combination with an anti-cancer or anti-viral agent. The anti-cancer or anti-viral agent may be a nucleoside/nucleotide reverse transcriptase inhibitor (nucleoside analog) such as 5' fluorouracil, fludarabine, cladribine, cytarabine, gemcitabine, capecitabine, troxacitabine, zidovudine/lamivudine (Combivir®), emtricitabine (Emtriva®), emtricitabine (Epivir®), zalcitabine (Hivid®) zidovudine (Retrovir®), abacavir/zidovudine/lamivudine (Trizivir®), didanosine (Videx®, VidexEC®), tenofovir disoproxil fumarate (Viread®), stavudine (Zerit®), or abacavir (Ziagen®).

Without being bound to any theory, it is hypothesized that the above anti-cancer agents operate by a mechanism similar to the anti-TK1 MAb. That is, cell proliferation requires replication. Like the anti-TK1 antibody, these anti-cancer agents interfere with the transformed cell's ability to replicate and therefore are useful in a method of treating both cancer and viral infection. The methods described herein may be used generally to treat abnormal cell proliferation, especially due to cancer or viral infection.

Thus, in alternative embodiments, anti-cancer agents such as nucleoside analogs are used to treat cancer. These methods are based upon the same mechanism as discussed above. That is, cell proliferation requires replication. Like the anti-TK1 antibody, these anti-cancer agents interfere with the transformed cell's ability to replicate and therefore are useful in a method of treating both cancer and viral infection. The methods described herein may be used generally to treat abnormal cell proliferation, especially due to cancer or viral infection.

Monoclonal Antibodies

Monoclonal antibodies (MAbs) are produced by the fusion of spleen lymphocytes with malignant cells (myelomas) of bone marrow primary tumors. Milstein, Sci. Am., 243, 66 (1980). The procedure yields a hybrid cell line, or hybridoma, arising from a single fused cell hybrid, or clone, which possesses characteristics of both the lymphocytes and myeloma cell lines. Like the lymphocytes (taken from animals primed with sheep red blood cells as antigens), the fused hybrids or hybridomas secrete antibodies (immunoglobulins) reactive with the antigen. Moreover, like the myeloma cell lines, the hybrid cell lines are immortal. Specifically, whereas antisera derived from vaccinated animals are variable mixtures of antibodies which cannot be identically reproduced, the single-type of immunoglobulin secreted by a hybridoma is specific to one and only one determinant on the antigen, a complex molecule having a multiplicity of antigenic molecular substructures, or determinants (epitopes). Hence, monoclonal antibodies raised against a single antigen may be distinct from each other depending on the determinant that induced their formation. However, all of the antibodies produced by a given clone are identical. Furthermore, hybridoma cell lines can be reproduced indefinitely, are easily propagated in vitro and in vivo, and can yield monoclonal antibodies in extremely high concentrations.

Monoclonal antibodies have largely been applied clinically to the diagnosis and therapy of cancer, the modulation of the immune response to produce immunosuppression for treatment of autoimmune and graft versus host diseases (GVHD) and for prevention of allograft rejection. Human monoclonal antibodies have also been applied clinically against breast cancer, cancers of the blood, cytomegalovirus, Varicella zoster virus, and the various specific serotypes of *Pseudomonas aeruginosa*, *Escherichia coli*, and *Klebsiella pneumoniae*.

Monoclonal antibodies useful in the present invention are produced using well known hybridoma fusion techniques (G. Kohler and C. Milstein, Eur. J. Immunol., 6, 511 (1976); M. Shulman et al., Nature, 276, 269 (1978)). As indicated above, preferred embodiments of the invention use a monoclonal antibody directed against TK1.

TK1 may be prepared by methods as described in U.S. Pat. No. 5,698,409, which is incorporated herein by reference. U.S. Pat. No. 5,698,409 describes a purified mammalian thymidine kinase 1 (TK1) from Raji cells. Raji cells are an immortalized human lymphoma cell line, available from ATCC as cell line #CCL-86. U.S. Pat. No. 5,698,409 also describes a monoclonal antibody to TK1.

The protein may also be prepared by chemical synthesis of all or part of the published protein sequence. For example, the protein sequence for human TK1 has been determined from the full length cDNA (MGC Program Team, "Generation and initial analysis of more than 15,000 full-length human and mouse cDNA sequences" PNAS (Dec. 24, 2002) vol. 99 (26): 16899-16903). The published protein sequence may be used to generate peptides that include all or part of the complete TK1 protein. These peptides may then be used to generate MAb's by means as described herein.

Alternatively, the TK1 protein may be produced recombinantly using a TK1 nucleotide sequence. The nucleotide sequence for human TK1 and the corresponding protein sequence are known to the art.

In some embodiments, it is preferred to humanize the anti-TK1 MAb. The humanized antibody can comprise portions derived from an immunoglobulin of nonhuman origin with the requisite specificity, such as a mouse, and from immunoglobulin sequences of human origin (e.g., a chimeric immunoglobulin), joined together chemically by conventional techniques (e.g., synthetic) or prepared as a contiguous polypeptide using genetic engineering techniques (e.g., DNA encoding the protein portions of the chimeric antibody can be expressed to produce a contiguous polypeptide chain). Another example of a humanized immunoglobulin of the present invention is an immunoglobulin containing one or more immunoglobulin chains comprising a CDR of nonhuman origin (e.g., one or more CDRs derived from an antibody of nonhuman origin) and a framework region derived from a light and/or heavy chain of human origin (e.g., CDR-grafted antibodies with or without framework changes). Chimeric or CDR-grafted single chain antibodies are also encompassed by the term humanized immunoglobulin.

Also included within the invention are humanized antibodies which have been veneered or reshaped. For example, the rodent variable region is compared to the consensus sequence of the protein sequence subgroup to which it belongs and the selected human constant region accepting framework is compared with its family consensus sequence. Idiosyncratic residues are replaced by more commonly occurring human residues.

Such humanized immunoglobulins can be produced using synthetic and/or recombinant nucleic acids to prepare genes encoding the desired humanized chain. For example, nucleic acid sequences coding for humanized variable regions can be constructed using PCR mutagenesis methods to alter DNA sequences encoding a human or humanized chain, such as a DNA template from a previously humanized variable region (see e.g., Kamman, M., et al., Nucl. Acids Res., 17: 5404 (1989)); Sato, K., et al., Cancer Research, 53: 851-856 (1993); Daugherty, B. L. et al., Nucleic Acids Res., 19(9): 2471-2476 (1991); and Lewis, A. P. and J. S. Crowe, Gene, 101: 297-302 (1991)). Using these or other suitable methods, variants can also be readily produced. In one embodiment, cloned variable regions can be mutagenized, and sequences encoding variants with the desired specificity can be selected (e.g., from a phage library; see e.g., Krebber et al., U.S. Pat. No. 5,514,548; Hoogenboom et al., WO 93/06213, published Apr. 1, 1993; Knappik et al., WO 97/08320, published Mar. 6, 1997)).

Alternatively, humanized antibodies may be conveniently prepared by injection of purified TK1 into SKID mice or other SKID animal which have accepted xenografts of adult human peripheral blood leukocytes as described in U.S. Pat. No. 5,476,996, which is incorporated herein by reference in its entirety. By this treatment, human immune function is introduced into the SKID animal which can be used to produce humanized antibodies.

Immunotoxins

Certain embodiments of the invention include the use of an immunotoxin linked to the anti-TK1 MAb. Several requirements must be fulfilled for an immunotoxin to be effective. First of all, the immunotoxin should be specific and should not react with tissues that do not express the target antigen to the extent that it is detrimental to the target mammal. Pastan et al., Cell, 47, 641 (1986). Binding to tissues that do not express antigen can be reduced by removal of the nonspecific natural cell-binding subunits or domains of the biotherapeutic moiety, e.g., a plant glycoprotein toxin or antiviral agent. Furthermore, because plant glycoprotein toxins contain mannose oligosaccharides that bind to cells of the reticuloendothelial system and, in some cases, also contain fucose residues that are recognized by the receptors on hepatocytes, deglycosylation of plant toxins may be required to avoid rapid clearance and potential cytotoxic effects on these cells. Secondly, the linkage of the toxin to the antibody should not substantially impair the capacity of the antibody to bind to the antigen. Third, the immunotoxin must be effectively internalized into the endosomic vesicles. Thus, toxins directed by monoclonal antibodies to surface receptors that are normally internalized may be more active than those directed toward non-internalizing cell surface molecules. Fourth, the active component of the toxin must translocate into the cytoplasm. Finally, for in vivo therapy, the linkage between the MAb and the toxin must be sufficiently stable to remain intact while the immunotoxin passes through the tissues of the mammal to its cellular site of action.

The activity of an immunotoxin is initially assessed by measuring its ability to kill cells with target antigens on their surfaces. Because toxins act within the cells, receptors and other surface proteins that naturally enter cells by endocytosis usually are appropriate targets for immunotoxins, while surface proteins that are fixed on the cell surface are not. However, if several antibodies recognizing different epitopes on the same cell surface protein are available, it is useful to test them all. This is because some antibodies, perhaps by producing a conformational change in the target protein, may more efficiently induce internalization or direct intracellular routing to an appropriate location for toxin translocation. May et al., Cell Immunol., 135, 490 (1991). Also, if the receptors are efficiently internalized, it is possible to employ an immunotoxin that does not bind as strongly to the receptor, due to the chemical modification(s) needed to prepare the immunotoxin. Willingham et al., Proc. Natl. Acad. Sci. USA, 84, 2474 (1987).

Toxins

An array of toxins of bacterial and plant origin have been coupled to MAbs for production of immunotoxins. The strategy is to select from nature a cytotoxic protein and then to modify the cytotoxic protein so that it will no longer indiscriminately bind and kill normal cells, but will instead kill only the cells expressing the antigen bound by the MAb. To be optimally effective, such an approach requires that internalization of relatively small numbers of cytotoxic molecules be lethal to target cells, as there are limited receptor sites on the cell surface for a given MAb. The toxins produced by certain bacteria and plants that inactivate cellular protein synthesis meet this criteria as, unlike most chemotherapeutic agents which act in a stoichiometric manner, they are catalytic in their lethal activity. In general, less than ten toxin molecules in the cytoplasm of a cell are sufficient to kill the cell.

Two classes of toxins that inactivate protein synthesis have been widely employed in the construction of immunotoxins. The first class consists of intact toxins, such as intact ricin. These toxins cannot be safely applied in vivo because of lethal toxicity. The second group of toxins are referred to as hemitoxins. Lethally inhibiting protein synthesis in a complementary manner, hemitoxins covalently modify the ribosome such that it can no longer productively interact with elongation factor 2. This latter family of toxins includes pokeweed antiviral protein (PAP), ricin, abrin, gelonin, saporin, and alpha-sarcin. The ribosome inactivating proteins derived from plants consist of either two chains, including a binding chain and catalytic chain (e.g., ricin), or a single catalytic chain alone (e.g., PAP or saporin).

In certain embodiments, anti-TK1 antibody immunotoxins for use in the present method are formed by linking an effective cytotoxic or anticancer amount of immunotoxin molecules to each molecule of anti-TK1 antibody. For example, a reagent useful in the practice of the invention includes one to two immunotoxin molecules per anti-TK1 antibody molecule. Preferably, a composition of the invention includes about a 1:1 mixture of a) one molecule of immunotoxin/molecule of anti-TK1 antibody, and b) two molecules of immunotoxin/molecule of anti-TK1 antibody. Preferably, a composition of the invention contains mainly 1 or 2 immunotoxin molecules per intact anti-TK1 monoclonal antibody molecule, free anti-TK1 monoclonal antibody, and free immunotoxin.

Modes of Administration of Anti-TK1 MAb or Anti-TK1 Antibody Immunotoxin

The anti-TK1 MAb or anti-TK1 antibody immunotoxin of the invention, or a combination thereof, can be formulated as a pharmaceutical composition and administered to a human or other mammal with cancer, preferably as a unit dosage form comprising an effective amount of one or more of the anti-TK1 MAb or anti-TK1 antibody immunotoxin in combination with a pharmaceutically acceptable carrier or vehicle, and/or in combination with other therapeutic agents.

Dosage Forms

It is preferred that the anti-TK1 MAb or anti-TK1 antibody immunotoxin of the present invention be parenterally administered, i.e., intravenously, or subcutaneously by infusion or injection. Solutions or suspensions of the biotherapeutic agent can be prepared in water, or a physiological salt solution such as isotonic saline or PBS, optionally mixed with a non-toxic surfactant.

Although it is preferred that the anti-TK1 MAb or anti-TK1 antibody biotherapeutic agent be administered as a liquid composition as described herein, it can be administered with a variety of other carriers. For example, dispersions can also be prepared in glycerol, liquid polyethylene glycols, DMA, vegetable oils, triacetin, and mixtures thereof. Under ordinary conditions of storage and use, these preparations may contain a preservative to prevent the growth of microorganisms. Additionally, more specific delivery of the anti-TK1 MAb or anti-TK1 antibody biotherapeutic agent to the lungs may be accomplished via aerosol delivery systems.

The compositions suitable for injection or infusion can include sterile aqueous solutions or dispersions or sterile powders comprising the anti-TK1 MAb or anti-TK1 antibody biotherapeutic agent which are adapted for the extemporaneous preparation of sterile injectable or infusible solutions or dispersions. In all cases, the ultimate composition must be sterile, fluid and stable under the conditions of manufacture and storage. The liquid carrier or vehicle can be a solvent or liquid dispersion medium comprising, for example, water, ethanol, a polyol (for example, glycerol, propylene glycol, and liquid polyethylene glycols, and the like), vegetable oils, nontoxic glycerol esters, lipids (for example, dimyristoyl phosphatidyl choline) and suitable mixtures thereof. The proper fluidity can be maintained, for example, by the formation of liposomes, by the maintenance of the required particle size in the case of dispersion or by the use of nontoxic surfactants. The prevention of the action of microorganisms can be accomplished by various antibacterial and antifungal agents, for example, parabens, chlorobutanol, phenol, sorbic acid, thimerosal, and the like. In many cases, it will be desirable to include isotonic agents, for example, sugars, buffers or sodium chloride. Prolonged absorption of the injectable compositions can be brought about by the inclusion in the compositions of agents delaying absorption, for example, aluminum monostearate hydrogels and gelatin.

Sterile injectable or infusable solutions are prepared by incorporating the anti-TK1 MAb or anti-TK1 antibody biotherapeutic agent in the required amount in the appropriate solvent with various of the other ingredients enumerated above, and as required, followed by filter sterilization. In the case of sterile powders for the preparation of sterile injectable or infusable solutions, the preferred methods of preparation are vacuum drying and the freeze drying techniques, which yield a powder of the active ingredient plus any additional desired ingredient present in the previously sterile-filtered solutions.

Furthermore, suitable formulations for the anti-TK1 MAb or anti-TK1 antibody biotherapeutic agent of the present invention include those suitable for oral, rectal, nasal, topical (including, ocular, and sublingual) or vaginal administration or in a form suitable for administration by inhalation or insufflation. The formulations may be prepared by any of the methods well known in the art of pharmacy. Such methods include the step of bringing into association the biotherapeutic agent with liquid carriers or finely divided solid carriers or both and then, if necessary, shaping the product into the desired formulation.

Pharmaceutical formulations suitable for oral administration may conveniently be presented as discrete units such as capsules, sachets, or tablets, each containing a predetermined amount of the active ingredient; as a powder or granules; as a solution, a suspension or as an emulsion. The active ingredient may also be presented as a bolus, electuary or paste. Tablets and capsules for oral administration may contain conventional excipients such as binding agents, fillers, lubricants, disintegrants, or wetting agents. The tablets may be coated according to methods well known in the art. Oral liquid preparations may be in the form of, for example, aqueous or oily suspensions, solutions, emulsions, syrups or elixirs, or may be presented as a dry product for constitution with water or other suitable vehicle before use. Such liquid preparations may contain conventional additives such as suspending agents, emulsifying agents, non-aqueous vehicles (which may include edible oils), or preservatives.

The biotherapeutic agent of the present invention may also be formulated for intra-nasal or ocular administration. In this form of administration, the active ingredient may be used as a liquid spray or dispersible powder or in the form of drops. Drops, for example, eyedrops, may be formulated with an aqueous or non-aqueous base also comprising one or more dispersing agents, solubilizing agents or suspending agents. Liquid sprays are conveniently delivered from pressurized packs.

For administration by inhalation, the biotherapeutic agent is conveniently delivered from an insufflator, nebulizer or a pressurized pack or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount.

Alternatively, for administration by inhalation of insufflation, the biotherapeutic agent may take the form of a dry powder composition, for example, a powder mix of the compound or a suitable powder base such as lactose or starch. The powder composition may be presented in unit dosage form in, for example, capsules or cartridge or e.g., gelatin or blister packs from which the powder may be administered with the aid of an inhaler or insufflator.

Additionally, the anti-TK1 MAb or anti-TK1 antibody biotherapeutic agent of the present invention is well suited to formulation in controlled release dosage forms. The formulations can be so constituted that they release the active dry ingredient only or preferably in a particular physiological location, optionally over a period of time. The coatings, envelopes, and protective matrices may be made, for example, from polymeric substances or waxes. The compounds can also be delivered via patches for transdermal delivery, subcutaneous implants, infusion pumps or via release from implanted depot sustained release dosage forms.

Dosages

The dosage of the biotherapeutic agents in the compositions of the invention can be varied widely, in accord with the size, age and condition of the mammal and the disease. Dosages are administered with a frequency based on the plasma half life of anti-TK1 MAb or anti-TK1 antibody biotherapeutic agent in a given patient. Higher doses can be employed in some cases, and the doses can readily be adjusted to provide appropriate amounts of the biotherapeutic agent to children.

EXAMPLES

Example 1

Assay of Raji Cells for TK1 Activity

One method of preparing TK1 and TK1 monoclonal antibody is the method essentially as described in U.S. Pat. No. 5,698,409, which is incorporated herein by reference. A crude cell extract was prepared from Raji cells (human Burkitt's lymphoma, American Type Culture Collection (ATCC) CCL 86) as follows. Approximately $10^{11}$ to $10^{12}$ exponentially-growing Raji cells were harvested by centrifugation from the growth medium. The pelleted cells were separated from the supernatant and resuspended in 1-2 mls of extraction buffer containing 0.02M Tris-HCl, pH 7.8, 0.05M $MgCl_2$, and 0.2 mM KCl. The cell suspension was subjected to three freeze-thaw cycles in liquid nitrogen and a 37° C. water bath. The ruptured cell suspension was then centrifuged at 30,000×g for 30 minutes at 4° C. to pellet cellular debris. The supernatant, containing about 50 mg/ml of protein, including TK and other soluble enzymes, was decanted from the pellet and stored frozen at −20° C.

To perform TK assays, 0.2 ml of the crude extract was mixed with an equal amount (0.2 ml) of an assay mixture containing 0.02M Tris-HCl (pH 7.8), $2\times10^{-6}$ M $[^3H]$-thymidine (85 curies per mmole), 0.002M $MgCl_2$, 0.2M KCl, 0.1M $NH_4Cl$, 0.005M mercaptoethanol, and 0.004M ATP (adenosine triphosphate).

The assay reactions were incubated at 37° C. in a water bath. After 30 minute and 60 minute incubation periods, 0.025 ml samples were removed and spotted onto Whatman DE-81 discs and allowed to dry. The filter discs were washed three times with 0.01M formate for 5 minutes each time, rinsed with distilled water for 5 minutes, followed by rinsing with methanol, and then transferred to scintillation vials containing 4 mls of scintillation counting fluid for measurement of $^3H$ radioactivity.

Example 2

Partial Purification of TK1

TK1 enzyme was partially purified from the crude extract of Raji cells of Example 1 by DEAE-cellulose anion exchange chromatography. To obtain the largest yields of TK protein, it is desirable that the cells be in the exponential growth phase when harvested. The protein content of the crude extract was determined using the well-known Bradford assay. A total of about 1.0-2.0 grams of protein from the crude extract was added to a DEAE-cellulose column and washed with 10 void volumes of 0.1M Tris-HCl (pH 8.0) using gravimetric flow. The column was eluted with 0.5M Tris-HCl (pH 8.0), and 1.0 ml fractions were collected.

A chromatograph of the absorbance measured at 280 nm as a function of elution time was produced. Aliquots of the collected fractions were assayed for TK1 activity generally as described in Example 1. Multiple runs were pooled and were concentrated using an Amicon protein concentrator.

Example 3

Purification by FPLC

An FPLC column (Pharmacia MONO-Q 5/5 anion exchange column) was loaded with 0.1 ml of the concentrated DEAE-cellulose fraction, described above, containing about 1 mg protein, and voided with 10 volumes of Buffer A (50 mM Tris-HCl pH 8.0). A programmed gradient was set up to gradually increase the concentration of Buffer B (1.0M NaCl, 50 mM Tris-HCl, pH 8.0) from 0-100% over 20 minutes running at a constant flow rate of 1.0 ml/min.

The protein was detected as it eluted from the column by absorbance at 280 nm. Fractions containing the 280 nm absorbance peaks were collected and assayed for TK1 activity as described previously herein.

The fractions having TK1 activity from several runs were collected, pooled and concentrated. This partially purified, pooled sample was then re-run on the MONO-Q column with a lower gradient. One-tenth ml portion of pooled sample containing about 1 mg protein was loaded on the MONO-Q column as before. For this second run, the gradient was started at 5% of Buffer B and ran to 40% Buffer B over 35 minutes at 1.0 ml/min.

A chromatogram of absorbance vs. elution volume for the second sequential MONO-Q run was produced. Fractions containing 1.0 ml of elutant were again collected as determined by assay for TK1 activity.

A third sequential MONO-Q run was performed on protein precipitated and pooled from the second column above. The running conditions were further changed by slowing the flow rate and further decreasing the gradient. A gradient of 5% Buffer B to 30% Buffer B was run at 0.5 mls/min. For this run, 0.5 ml fractions were collected.

Example 4

Production of Monoclonal Antibodies Binding to TK1

Hybridoma cell lines producing antibodies to TK1 were produced by methods generally known in the art, but with certain modifications. The description of the development of monoclonal antibodies using a particular hybridoma cell line is only exemplary. Embodiments of the invention contemplate the use of a battery of clones produced by various means such as the use of hybridoma cell lines and other recombinant techniques.

TK1 was prepared as described above. A dose of 100 µg of TK1 suspended in 50 µl of phosphate buffered saline (PBS) and 50 µl complete Freund's adjuvant was given intraperitoneally (I.P.) to each of a group of female BALB/c mice, 5-6 weeks old. Two weeks later, a second immunization was given that was identical to the first.

Two weeks following the second immunization with semi-pure TK1, an intrasplenic injection was given which contained 10 µg of pure active TK1 (prepared as described above) suspended in 100 µl of PBS. The mice were anesthetized with sodium pentobarbital (65 mg/ml) which was diluted by adding 6.7 mls to 93.3 mls of PBS. Each mouse was given 10 µl/gram of body weight I.P. Surgical intervention was performed using a scalpel and forceps, and the spleen was gently teased out for administration of the antigen. Several areas of the spleen were injected to ensure uniform distribution of the antigen. The wound was closed with metal sutures and the mice were placed under a heating lamp for 1-2 hours.

Seventy-two hours following the intrasplenic injection, the mice were sacrificed using ether and the spleen was removed. Before the mice were killed, blood was removed and the serum tested to ensure that the mice were mounting an immune response to the TK1 protein. The B cells were isolated from the spleen for fusion with an immortal myeloma cell line.

The cell line used for the fusion partner was a self-fused Sp2/0 line designated FO which was purchased from ATCC. It is a derivative of P3-X63-Ag8. This line is an immortal myeloma mouse cell line that is fast growing and a non-secretor (heavy or light chain immunoglobulins). The fusion of FO and activated spleen cells was performed generally as known in the art. One spleen containing about $1 \times 10^8$ cells was used per fusion. After the fusion was terminated, the fusion cell suspension was seeded into 96-well microtiter plates which had been seeded a day earlier with 3,000 to 6,000 mouse macrophages per well as feeder cells.

HAT selection medium was used to select only fusion products. Wells were marked for growth and gradually weaned out of HAT and into regular media. By this time the only surviving cells were hybridomas obtained by fusion of B-cells and FO cells. A total of about 500 colonies representing fusion products resulted from each fusion.

For use in tests with patient samples, the selected antibody-producing cell lines were passaged and supernatant was aseptically collected over a period of three months. Antibodies were purified by precipitating the supernatants with ammonium sulfate followed either by gel filtration chromatography or by DEAE-cellulose chromatography (diethylaminoethyl cellulose, obtained from Whatman International, Maidstone, Kent, UK under the tradename SEPHADEX). The antibodies were purified by standard methods and conjugated with either HRP-peroxidase or alkaline phosphatase (Bio-Rad). Such procedures are described in ANTIBODIES: A Laboratory Manual, by Harlowe and Lane, 1988.

The above-described method may be used with any TK1 protein as the antigen, including TK1 produced by chemical synthesis from the known protein sequence or from a recombinant protein produced by well-know methods using all or part of the known coding sequence of TK1.

Example 5

Production of Humanized Monoclonal Antibodies Binding to TK1

Human peripheral blood leukocytes are injected intraperitoneally into SCID mice as described in U.S. Pat. No. 5,476,996, which is incorporated herein by reference. About 2 weeks later, the SKID mice are immunized with human TK1. MAb are then obtained as described above in Example 4 or by recombinant techniques.

Example 6

Preliminary Screening of Hybridoma Colonies from Fusion

Five hundred colonies from one fusion were subjected to preliminary screening by ELISA against partially purified TK1 prepared as in Example 2. Supernatants collected from the hybridoma cultures were initially screened with semi-pure TK1 prepared by running the crude extract of Raji cells on DEAE cellulose to partially purify the TK1. Thus, this preliminary screen is used as an initial detection of antibodies immunoreactive with TK1.

Multiwell plates were coated with 1.0 µg (micrograms) per well of selected TK1 protein preparations suspended in 50 µl PBS, and allowed to dry overnight. The plates were then treated for 30 minutes with 200 µl per well of PBS-TWEEN 20®-EDTA-1% milk fat to block non-specific binding. The plates were washed three times with 200 µl of PBS-TWEEN 209 EDTA (PBST2E). (TWEEN 20® is an anionic detergent commercially available from Bio-Rad Laboratories, Richmond, Calif., and useful to reduce non-specific antibody-antigen binding while not disrupting binding of primary antibodies to antigens or of antigens to nitrocellulose.)

The growth medium on the hybridoma cell cultures was not changed for three days prior to collection of the hybridoma culture supernatants in order to saturate the media with antibodies. For each hybridoma, 80 µl of supernatant per well was added to duplicate wells. The multiwell plates were then incubated at 37° C. for one and a half hours. The supernatant was decanted and the wells washed six times with PBST2E.

Next, goat anti-mouse IgG (heavy and light chain specific) conjugated with peroxidase (available from Bio-Rad) and diluted 1:3,000 in PBST2E was added. One-tenth ml was added to each well and the plates incubated as before. The wells were again washed in PBST2E and 200 µl of substrate, tetramethyl-benzidine, was added and incubated for 1 hour. The substrate reaction was stopped by adding 50 µl of 2M sulfuric acid to each well to cause a color shift from blue to yellow. The plates were scanned for O.D. measurement at 450 nm on a plate reader. O.D. readings that were at least twice the background O.D. were deemed positive. Of about 25,000 clones obtained from fifty fusions, 35 tested positive in the preliminary screening. The positive colonies were isotyped using a kit from Hyclone, Logan, Utah (cat. # EK-5051), and the positive colonies were determined to produce antibodies of IgG1, IgG2a, IgG3, and IgM classes.

Example 7

Additional Screening for TK1-Specific Hybridomas

The 35 clones which tested positive in the initial screenings were subjected to more rigorous screening. A plate was coated with five pairs of replicate wells as follows: wells A, B were coated with a crude extract of TK1 from Raji cells; wells C,D were coated with TK1 prepared from the DEAE-cellulose column; wells E,F were coated with purified TK1 from peak 400 prepared as in Example 4 by FPLC; wells G,H were coated with TK1 protein from fractions 308, 310 of the second FPLC run; and wells J,K were coated with an extract of *E. coli* cells which expressed a TK1 gene in a PET vector. For the purified samples, 1.0 µg per well of protein was used.

The ELISA was performed essentially as described for the preliminary screening. Of the 35 clones tested, one proved to bind only to active form TK1. The absorbance readings (ABS) were made at 405 nm for 120 wells on one plate on which ten clones were screened. The clones testing most highly positive by preliminary screening were purposely clustered on this plate. The background ABS from four wells was averaged and found to be about 0.058 (wells J11, J12 and K11, K12).

It will be apparent that positive binding (absorbance significantly greater than the background level) was observed in all the wells in columns 2 and 5; in all but rows C,D of column 1; in rows J,K of columns 3, 4 and 7; and in rows A,B of columns 4 and 7. That is, the clones in columns 1-5 and 7 all tested positive for binding to TK1. Of these, clones 2 and 5 tested positive for binding to all of the TK1 preparations tested, while clone 1 bound to all the TK1 preparations except the semi-purified DEAE-cellulose preparation. Clones 4 and 7 bound to the crude Raji cell TK1 extract and to the TK1 produced by genetic engineering in *E. coli*. Clone 3 bound only to the TK1 produced from *E. coli*. The remaining 25 clones tested negative for antibodies to TK1.

Example 8

Western Blot Analysis

Further characterization was performed by Western blotting. Western blots were prepared by procedures similar to those described in Current Protocols in Immunology, Vol. 1, publ. Wiley-Interscience, New York (1991). FIG. 1 shows a Western blot assay showing TK1 specificity of clone 14F2. Samples were separated using a native or a partial denature 12% polyacrylamide gel. Polypeptides were then transferred onto a nitrocellulose filter and probed with MAb from clone 14F2. A conjugate antibody solution containing goat anti-mouse IgG (H1L chains) horseradish peroxidase was used to visualize MAb binding. (a) Lane 1, purified TK1, native sample, Ponceau S staining; Lane 2, purified TK1, native sample, Western blot. (b) Lane 1, purified TK1, partial denature sample, Ponceau S staining; Lane 2, Purified TK1, partial denature sample, Western blot; Lane 3, Raji cell extract, partial denature sample, Western blot; Lane 4, Hela cell extract, partial denature sample, Western blot.

Example 9

Inhibition of TK1 Activity by Selected Monoclonal Antibodies

Raji cells ($1\times10^6$) were harvested by centrifugation at 1500 rpms for 10 minutes. After discarding the supernatant, 1 ml of enzyme mix (1:10 0.02% β-mercaptoethanol:Tris-HCl pH 7.5) was added to the cells. The mixture was frozen in liquid nitrogen and the cells were then thawed in a 37° C. water bath. The freeze/thaw steps were repeated three times. Finally, the mixture was centrifuged at 14,000 rpms at 4° C. for 75 minutes to remove cell membranes. The pellets were discarded.

25 µl of the Raji cell extract was distributed in each of 6 eppendorf tubes. Dilutions of fresh hybridoma media: hybridoma supernatant were prepared totaling 125 µl in the following proportions: 1:2, 1:4, 1:16, 1:32, and 1:64. 125 µl of hybridoma media was used as a control. Either the dilutions or the control were added to each of the 6 eppendorf tubes. The samples were assayed for thymidine kinase activity using the thymidine kinase radioassay described in Example 1. The greater the inhibition by the antibodies in the hybridoma supernatant, the lower the thymidine kinase activity

Example 10

Membrane Bound Protein Staining Protocol

The following protocol was used for staining lymphocytes and other cell types. For lymphocytes, blood was harvested in heparin tubes and diluted 1:2 with balanced salt solution (PBS). 5 mls of Ficoll were placed in the bottom of a 15 ml conical vial (one conical vial for every 7 mls of diluted blood). The conical vials containing the lymphocytes were centrifuged at 1300 rpm for 20 minutes. After centrifugation, the buffy layer that is suspended on the surface of the Ficoll was removed with a pipet. Up to 7 mls of the lymphocyte solution was transferred into a fresh 15 ml conical vial and again diluted 1:2 using PBS. The samples were again centrifuged at 1500 rpms for 10 minutes. This wash step was repeated 2 times.

For cell lines, 20 mls of cells that are growing at a concentration of $5\times10^5$ to $1\times10^6$ were transferred to a conical vial and centrifuged at 1500 rpms for 10 minutes. The cell pellet was suspended in 2 mls of PBS. This wash step was repeated two times.

For the staining, after washing the cells twice, the cells were resuspended in 3% formaldehyde solution and incubated on ice for 10 minutes (this step fixed the cells, and inhibited cell activation and interaction). After ten minutes, the cells were centrifuged at 1500 rpms for 10 minutes. The supernatant was aspirated and the pellet containing the cells was resuspended in 2 mls of PBS and centrifuged again for 1500 rpm×10 min. The cells were washed in PBS two more times. After washing the second time, the supernatant was poured off, leaving a small amount of liquid in the bottom of the conical vial. 10 µl of FC block was added to the cells and the cells were resuspended in a small amount of PBS and the FC block.

The cells were incubated on ice for 10 min. Then, 2 mls of PBS was added and the cells were again centrifuged at 1500 rpm×10 min. This wash was repeated two times. After the second wash, the cells were resuspended in 10 mls of supernatant from the hybridoma cell line and incubated on ice and in the dark for 1.5 hours. The cells were then centrifuged at 1500 rpm for 10 min. and washed twice.

The secondary antibody was diluted (e.g. 10 µls of 2 mg/ml secondary antibody in 820 µls PBS) and 200 µls was added to each cell pellet after the final wash. The secondary antibody was incubated with the treated cells for one hour in the dark on ice. After 1 hour, the cells were removed from the ice and diluted with 2 mls of PBS. The cells were centrifuged and the supernatant was removed by aspiration. The cells were washed three times. The cells were resuspended in 100 µls of PBS and kept in solution until ready to view. 10 μls was transferred to a clean microscope slide and covered with a glass cover slip for viewing.

FIGS. 3-12 and 21-22 were produced using the aforementioned immunofluorescence techniques. As can be seen in the Figures, the cancer cells such as the Raji cells, MD-MBA-435, MD-MBA-231, PANC-1 (human pancreatic cancer cell line), HEP-G2 (human liver cancer cell line), and HELA cells (cervical cancer cells transformed by Human Papilloma Virus 16) are strongly labeled by the anti-TK1 antibody due to the presence of TK1 on the surface of the cancer cells. The normal lymphocytes are not labeled.

Example 11

Flow Cytometer

Additional assays demonstrate that selected monoclonal antibodies bind specifically to cells overproducing TK1. Flow Cytometer plots were utilized to further characterize the ability of anti-TK1 antibodies to specifically target cancer cells.

Flow Cytometer plots were produced utilizing methods known in the art. Utilizing a test tube method each sample was placed in two labeled 12×75 mm test tubes, one for the monoclonal antibody and the other for the appropriate control. Subsequently, $1 \times 10^6$ cells from the mononuclear cell preparation were placed in each test tube and centrifuge at 2-8° C. at 400-450×g for 4 min. The supernatant was aspirated and discarded. Then 200 μL monoclonal antibody working solution or 200 μL of control working solution was placed into the appropriately labeled test tubes. The reactions were vortexed gently. The reactions were incubated at 2-8° C. for 30-35 min. Following incubation each reaction mixture was washed with 1 mL of 2-8° C. wash medium and centrifuged at 2-8° C. at 400-450×g for 4 min. Each reaction was aspirated carefully and the supernatant was discarded. A vortex was used subsequently to disrupt cell pellets. The wash steps that followed incubation were repeated. After the second wash, the samples were aspirated carefully and the supernatant was discarded. Then 200 mL of GAM-FITC working solution or Avidin d-FITC working solution (for Biotin-labeled) was added to each cell pellet. The cell pellets were gently disrupted using a vortex. The cells were incubated at 2-8° C. for 30-35 min. At the end of 30 min., the cells were washed three times with 1 mL of 2-8° C. resuspension medium. Each centrifugation was carried out at 400-450×g for 4 min at 2-8° C. The sample was then aspirated carefully and the supernatant was discarded. The cell pellets were then gently disrupted using a vortex. The steps following the second incubation were repeated twice. After the third wash, the cells were resuspended by adding 1 mL of 2-8° C. resuspension medium to each test tube. The samples were transferred into appropriate containers for flow cytometry or fluorescence microscopy analysis. To ensure maximum viability, the stained cells were analyzed promptly.

Figure 13:
FIG. 13 shows normal human lymphocytes stained with CB001 antibody using fluorescence microscopy at 500×.
Figure 14:
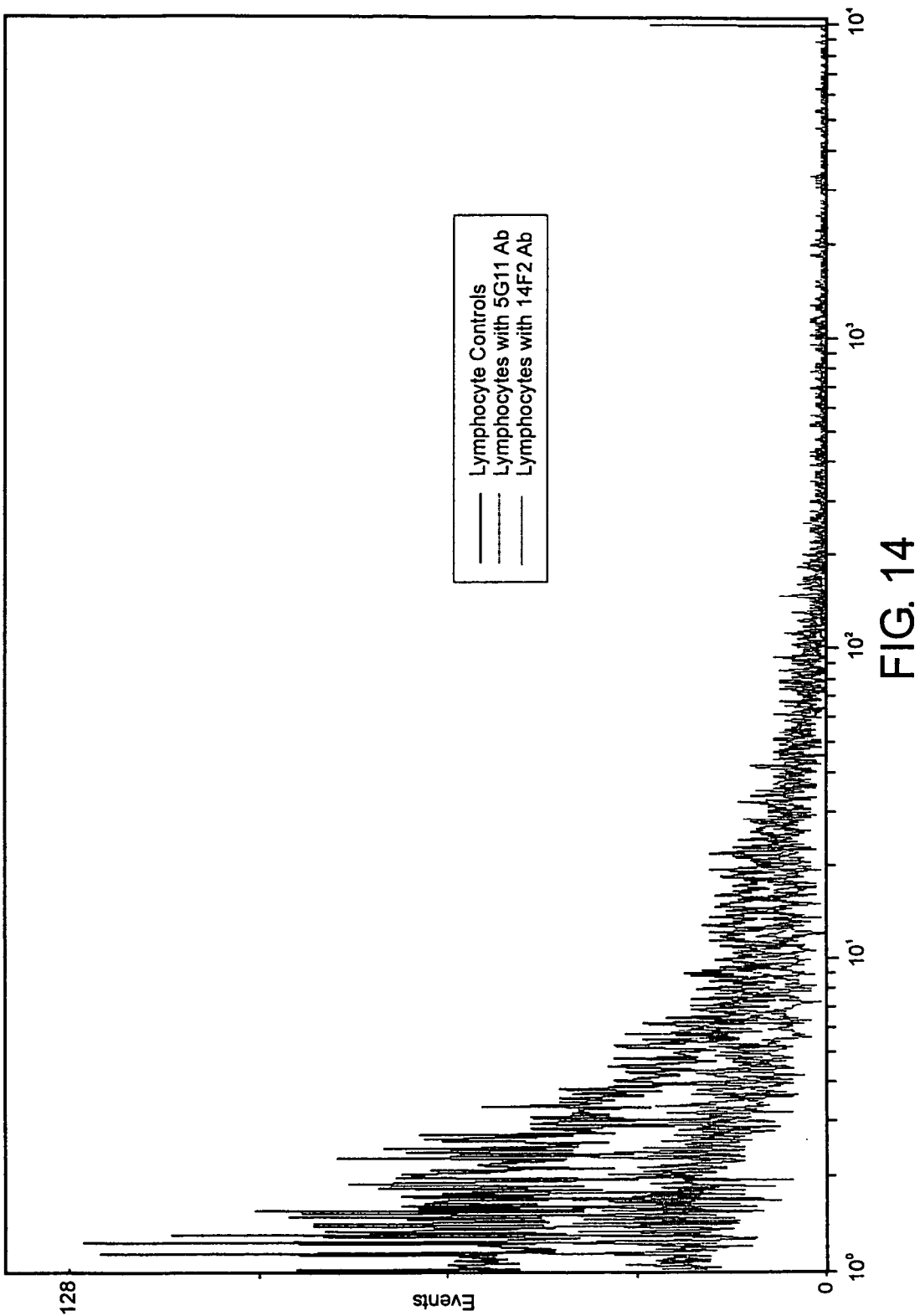
FIG. 14 shows cell counting of lymphocyte cells by flow cytometry. Lymphocyte control; lymphocytes stained with CB001 MAb to TK1; and lymphocytes stained with 14f2 MAb to TK1.
Figure 15:
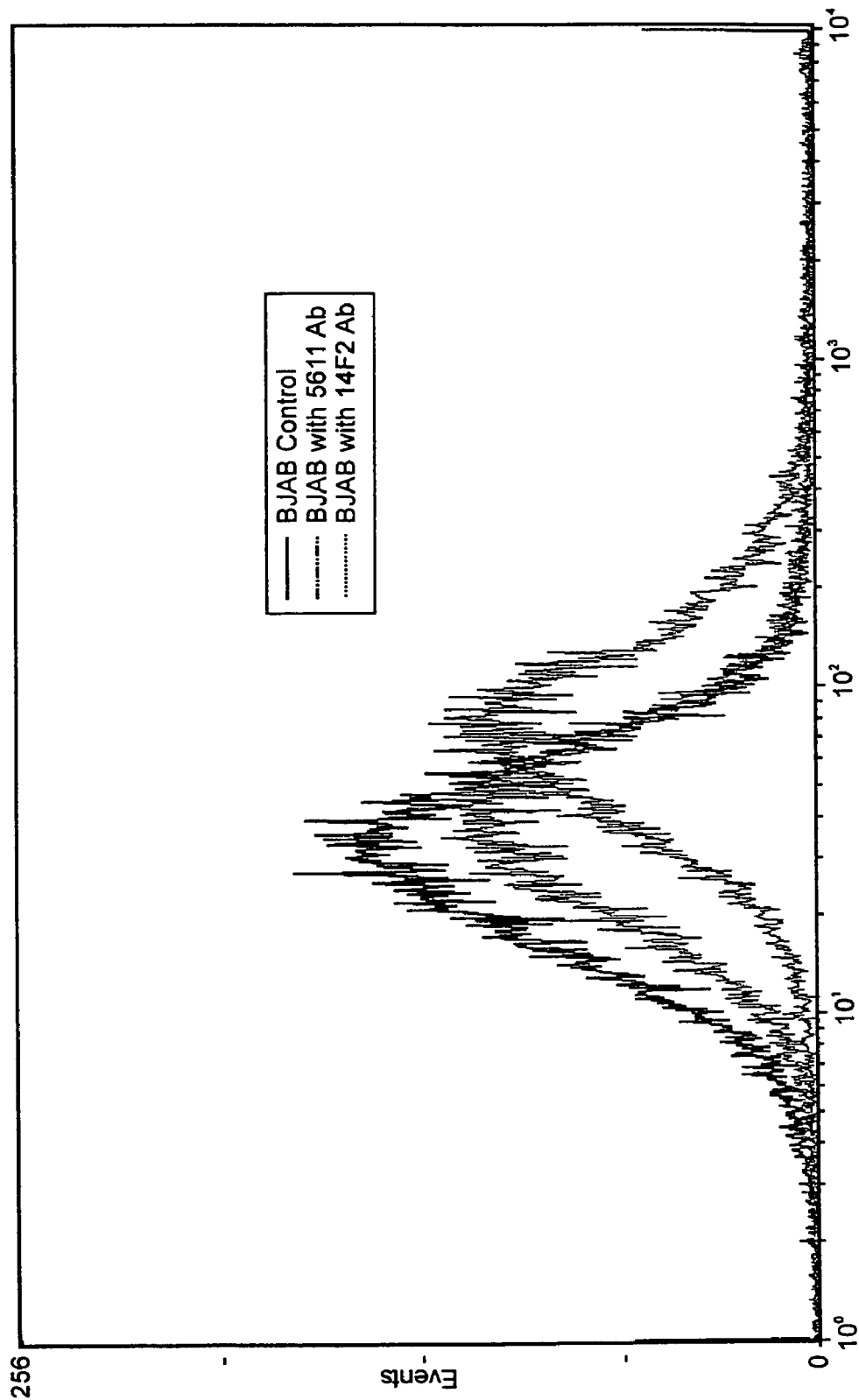
FIG. 15 shows cell counting of BJAB cancer cells by flow cytometry. BJAB control; BJAB cells stained with CB001 MAb to TK1; and BJAB cells stained with 14f2 MAb to TK1.

Blood was drawn from control patients without cancer to establish a baseline level against which to compare normal cells and known cancerous cell lines (FIG. 13-15). We first ran the lymphocyte controls through the Flow Cytometer without antibodies and 10.1% or 4,510 of 44477 total cells were counted by the Flow Cytometer, which sets the baseline level to compare unstained normal lymphocyte cells to lymphocyte cells stained with antibody. The results show that only 12.1% of the lymphocyte controls or 2494 of 20628 were counted by the Flow Cytometer when normal lymphocyte cells were incubated with CB001 monoclonal antibody, which does not differ significantly from the control number of 10.1% and demonstrates that TK1 is not detected by CB001 monoclonal antibody on the surface of the normal lymphocytes.

Additional Flow Cytometer plots were produced for BJAB cells (FIG. 23). The BJAB control cells were run through the Flow Cytometer without antibodies and only 6.64% or 1,448 of 20302 total cells were counted by the Flow Cytometer, which sets the baseline level to compare unstained BJAB cell to BJAB cells stained with antibody. The results show that 34.8% of the BJAB cells or 7055 of 20302 were counted by the Flow Cytometer when BJAB cells were incubated with CB001 monoclonal antibody, which, when compared to the control number of 6.64% demonstrates that TK1 is detected on the surface of the cancerous BJAB cell line.

Additional Flow Cytometer plots were produced for Human Burkett's Lymphoma (Raji) cells (FIG. 24). The Raji control cells were run through the Flow Cytometer without antibodies and only 10.3% or 2,051 of 1992 total cells were counted by the Flow Cytometer, which sets the baseline level to compare unstained Raji cells to Raji cells stained with antibody. The results show that 76.3% of the Raji cells were counted by the Flow Cytometer when Raji cells were incubated with CB001 monoclonal antibody, which, when compared to the control number of 10.3% demonstrates that TK1 is detected on the surface of the cancerous Raji cell line.

Similar results have also been obtained with other TK1 monoclonal antibodies raised against a chemically synthesized TK1 fragment prepared from 15 amino acids from the C-terminus of TK1.

Example 12

Anti-TK1 Utilized in Complement Mediated Lysis

In one therapeutic application for anti-TK1 monoclonal antibodies, the anti-TK1 antibody is useful for targeted tumor therapy. The bound anti-TK1 antibodies are utilized to initiate complement mediated lysis destroying the cancerous cells. This embodiment is particularly effective because the anti-TK1 antibody binds specifically to tumor cells expressing large amounts of TK1. Because the anti-TK1 antibody binds specifically to tumor cells expressing large amounts of TK1 it is targeted specifically to tumor cells and thus the killing of these tumor cells by complement mediated lysis is preferentially enhanced relative to the killing of normal cells. Additionally, TK1 unlike most other cancer markers, which are specific to only one type of cancer, acts as a useful cancer marker in many types of cancer. Complement mediated lysis is a process well known in the art. The selection of an appropriate complement pathway is within the knowledge of one skilled in the art and could be accomplished without the expense of undue experimentation.

Figure 16:
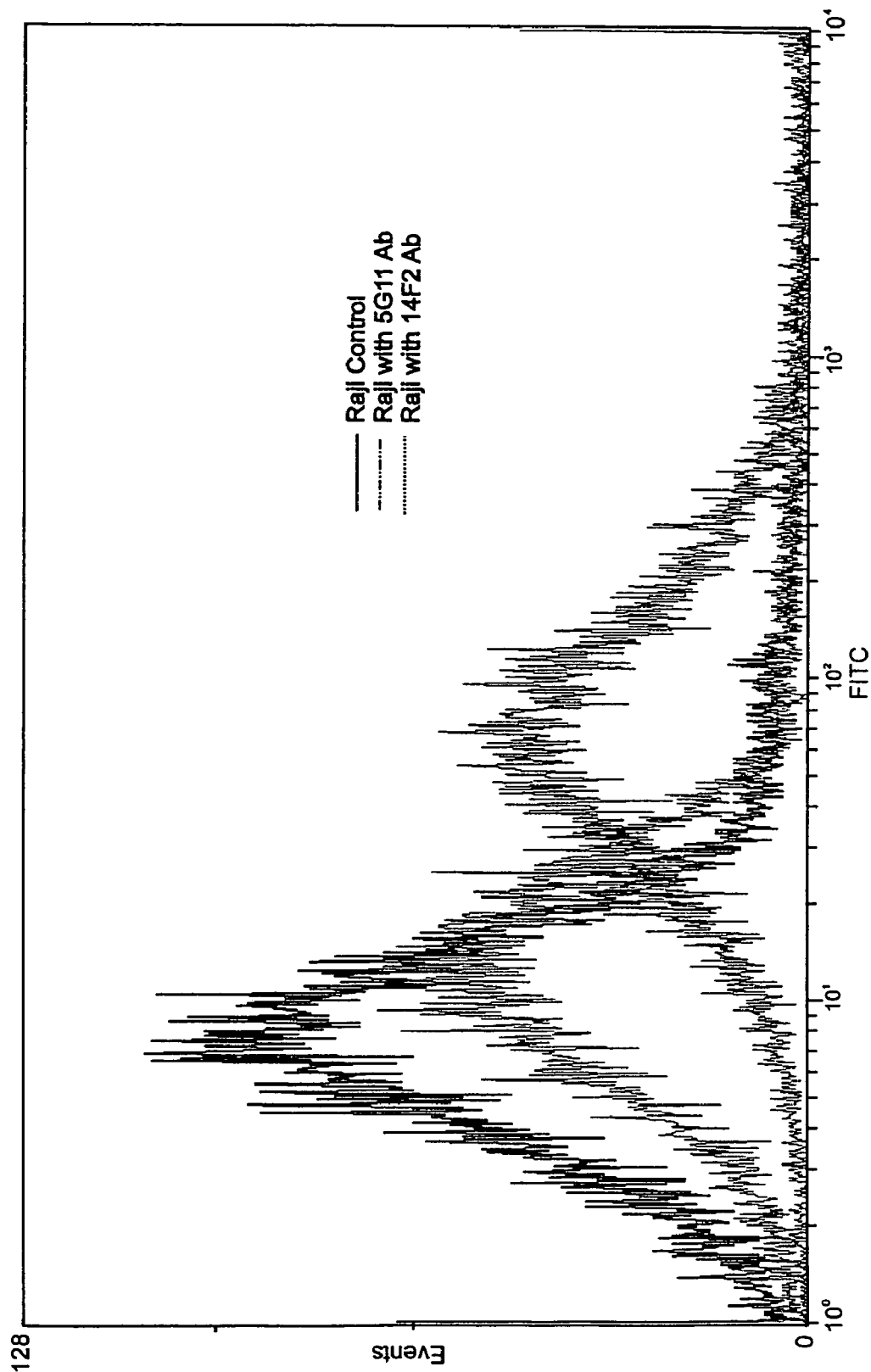
FIG. 16 shows cell counting of Human Burkitt's Lymphoma (Raji) cells by flow cytometry. Raji control; Raji cells stained with CB001 MAb to TK1; and Raji cells stained with 14f2 MAb to TK1.
Figure 17:
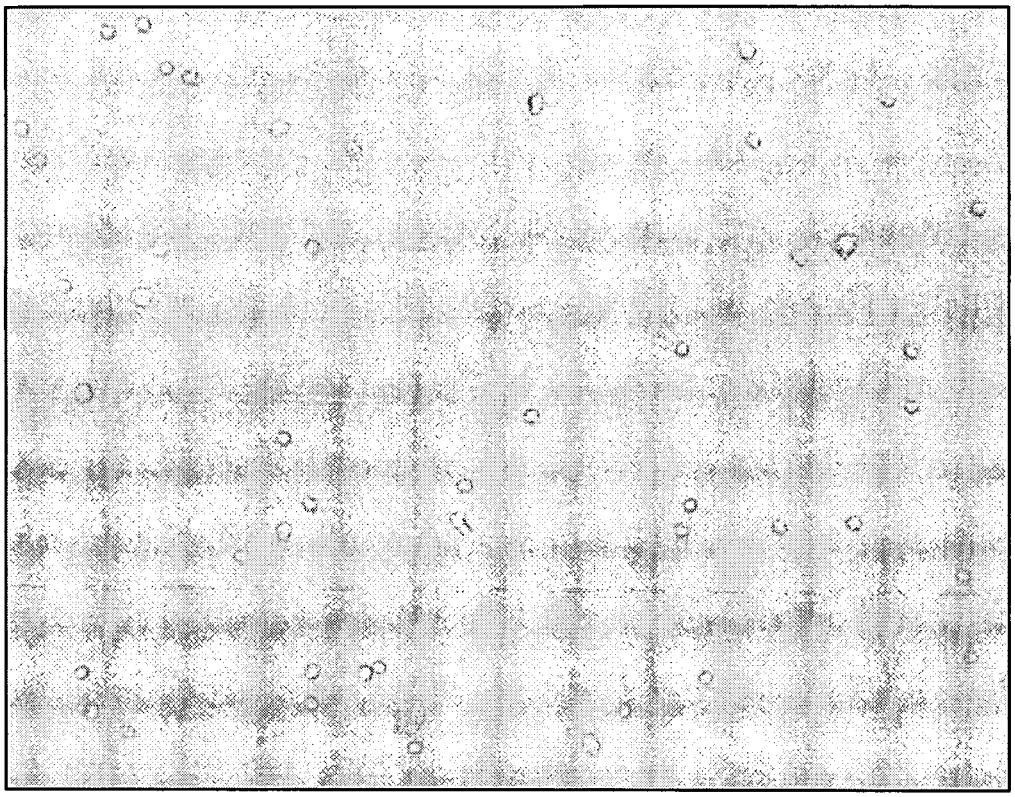
FIG. 17 shows Raji cells with CB001 Ab without serum—1.1 million cells/ml.

An example of a protocol for complement mediated lysis targeted by anti-TK1 has the following steps. First, 2 mls of Raji cells were removed from a culture kept between $5 \times 10^5$ and $1 \times 10^6$ cells per ml from culture. The cells were centrifuged at 1600 rpm for 10 minutes. The supernatant was discarded. Subsequently, the cells were washed three times with PBS. The hybridoma supernatant was diluted with PBS by a dilution factor of 1:2. The cells were then incubated in diluted supernatant for one hour on ice. After one hour the cells were washed three times and resuspended in one ml of PBS. Then 3 mls of serum were added to cells, and 3 mls of PBS to control cells. The cells were placed in a 37° water bath for one hour. The cells were subsequently removed from the water-bath and placed on a microscope slide for observation. FIGS. 16 and 17 are photos produced utilizing the aforementioned protocol.

Figure 18:
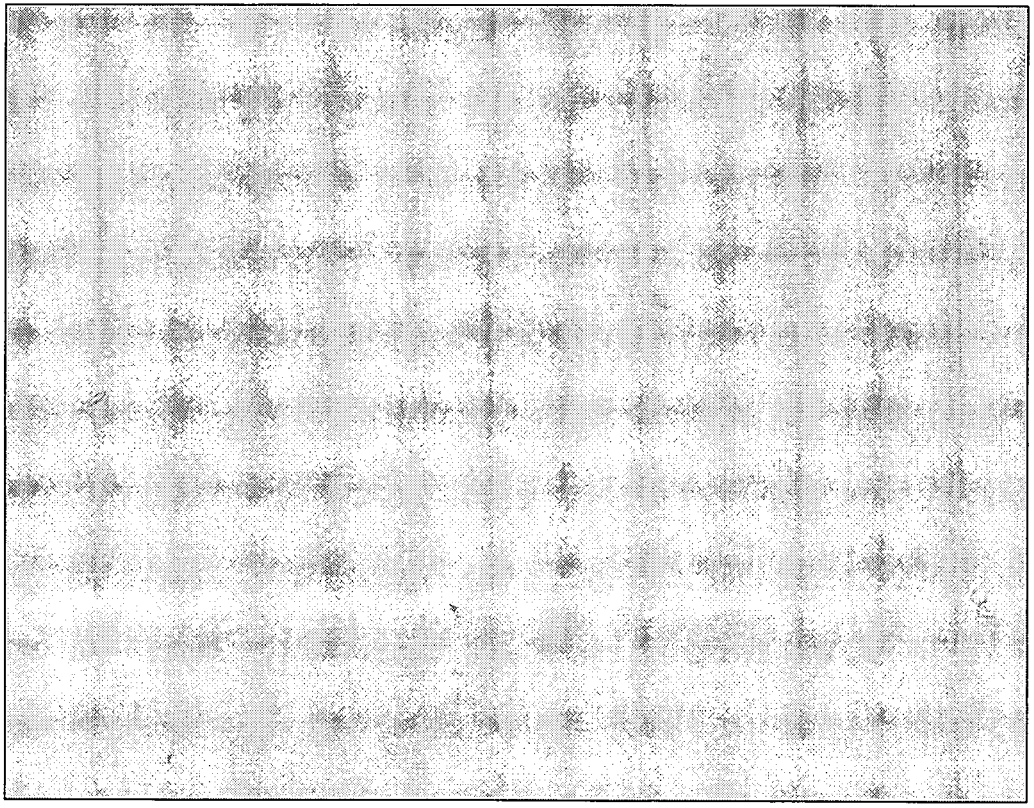
FIG. 18 shows Raji cells with CB001 Ab with serum.

FIGS. 17 and 18 demonstrate that cancerous B cells (Raji) are lysed by complement when TK1 antibody binds to the surface. FIG. 17 is a picture of the control Raji cells, and FIG. 18 is a picture of the cancerous B cells (Raji) destroyed by complement mediated lysis. Cell lysis was more than 96%.

Figure 19:
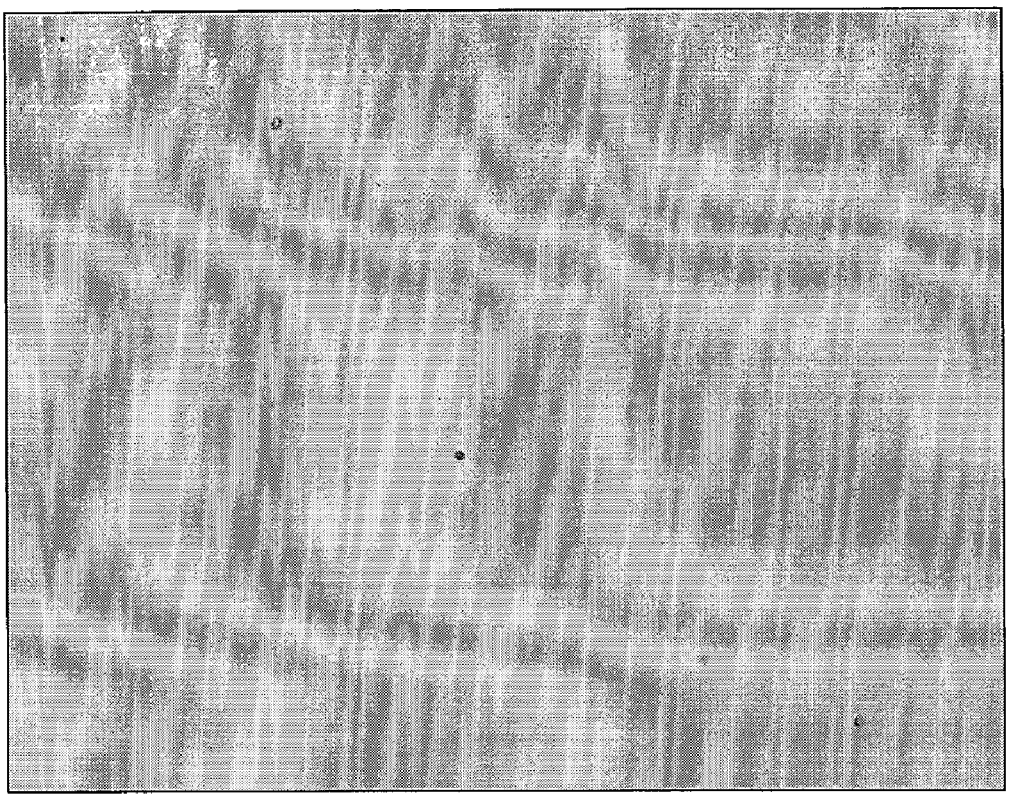
FIG. 19 shows human lymphocytes with CB001 antibody without serum.
Figure 20:
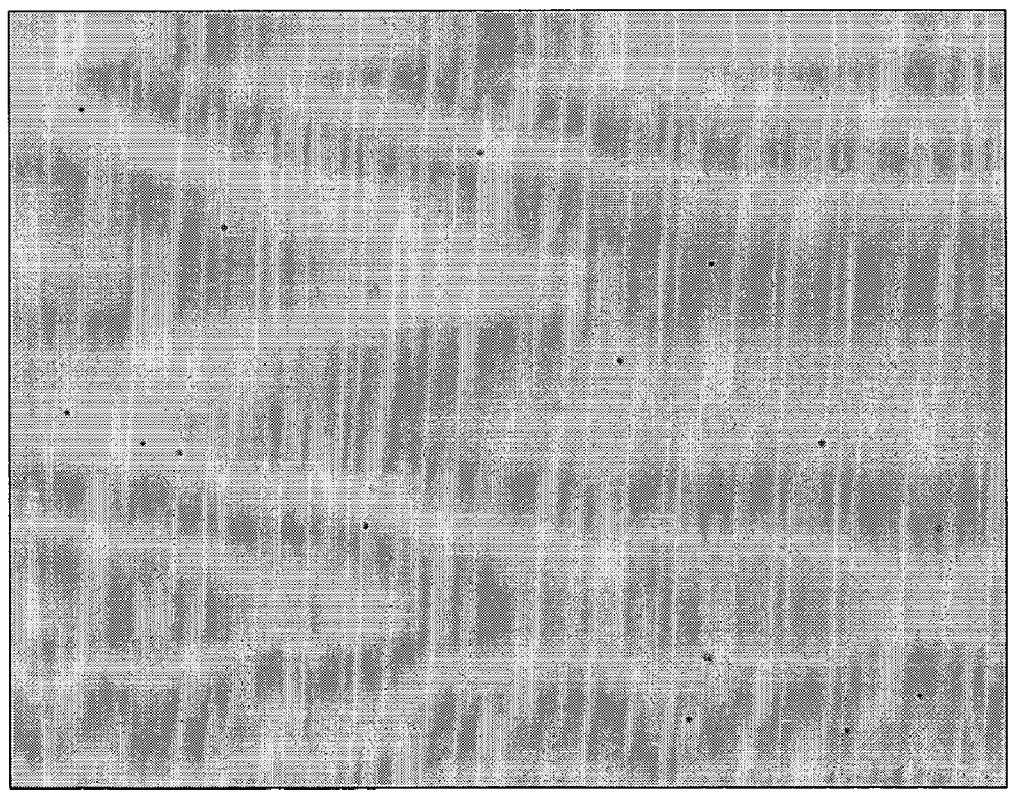
FIG. 20 shows human lymphocytes with CB001 antibody and serum. No measurable lysis.
Figure 21:
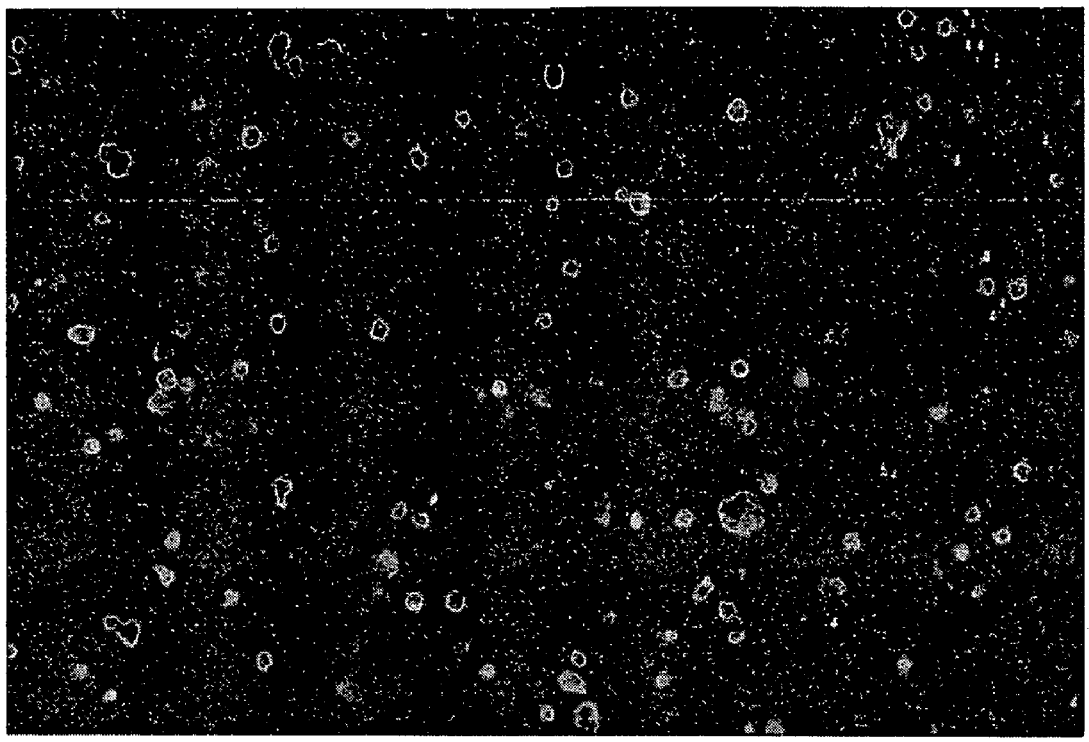
FIG. 21 shows HELA cells (cervical cancer cells transformed by Human Papilloma Virus 16) at 100× magnification.
Figure 22:
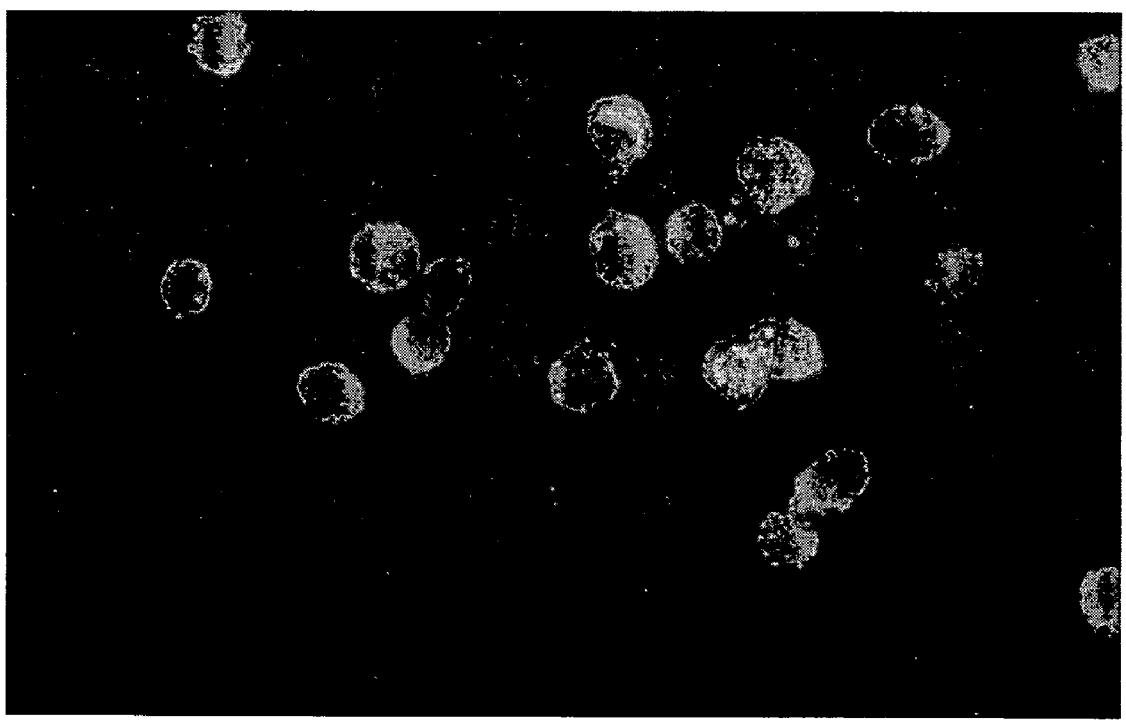
FIG. 22 shows HELA cells (cervical cancer cells transformed by Human Papilloma Virus 16) at 400× magnification.

FIG. 19 shows non-cancerous human lymphocytes with the CB001 antibody and without serum. FIG. 20 shows the non-cancerous human lymphocytes with CB001 and with serum. As can be seen, there is no lysis if the cell is not cancerous, even in the presence of the serum and the antibody. Only the cancerous cells were destroyed because of the expression of TK1.

Example 13

Utilizing Anti-TK1 to Target and Destroy Cancerous Cells

A variety of therapeutic applications are possible based on the knowledge that TK1 is found on the surface of cancerous cells. For example, it is possible that an anti-cancer drug might selectively target and kill cells expressing TK1 on the cell surface. This tactic is exemplified by cancer therapies that use Adenoviruses to infect cells with a plasmid that encodes a viral TK1 gene, which then could be targeted to be killed by interrupting DNA synthesis. This embodiment is further exemplified by the therapeutic application of anti-TK1 antibodies, which comprises anti-TK1 antibodies coupled with anti-tumor agents. An anti-tumor agent is coupled to the anti-TK1 antibody, which enhances the cytotoxic effects of the anti-TK1 antibody, and thus the killing of tumor cells relative to the killing of normal cells.

Example 14

Therapeutic Site Directed Surgery

Another therapeutic application contemplated by this invention is the use of anti-TK1 antibody, which may also be useful for site directed surgery. Dye and isotope directed surgeries are techniques known to those skilled in the art. Because anti-TK1 antibodies adhere to the surface of cancerous cells, this invention further contemplates using anti-TK1 antibodies to clearly mark cancerous tissues so that the infected tissues can be identified, visually or otherwise, by a surgeon who would then be able to excise or destroy the tissue utilizing minimally invasive surgical techniques. An appropriate dye is attached to the anti-TK1 MAb. For example, anti-TK1 antibodies are labeled with PET isotopes ($^{18}F$, $^{124}I$, or $^{76}Br$) or a radio-opaque dye, e.g., an iodine compound, barium or barium sulfate or gastrografin and the like.

Injectable antibodies also possess diagnostic and prognostic applications. In one embodiment, anti-TK1 antibodies tagged to a radioactive or a radio-opaque dye are injected into the patient. After the anti-Tk1 antibody has bound neoplastic tissue it is visualized using well known techniques such as PET, MRI, CT, SPECT, etc (see Molecular Imaging of Gene Expression and Protein Function In Vivo With PET and SPECT, Vijay Sharma, PhD, Gary D. Luker, MD, and David Piwnica-Worms, MD, Ph.D., JOURNAL OF MAGNETIC RESONANCE IMAGING 16:336-351 (2002)). The location and extent of spread of the disease facilitates medical diagnosis of cancer type, location, and stage.

Example 15

Kits which Utilize Monoclonal Antibodies for Therapeutic Purposes

Further, the invention contemplates using methods and kits for performing the methods. A kit for performing the above methods may comprise one or more monoclonal anti-TK1 antibodies. In one embodiment, the monoclonal antibody would be conjugated with or packaged in conjunction with other agents, for example immunotoxins or commercially available complement, that when used would have therapeutic effects on the intended patients.

It will be understood by those of skill in the art that numerous and various modifications can be made without departing from the spirit of the present invention. Therefore, it should be clearly understood that the forms of the present invention are illustrative only and are not intended to limit the scope of the present invention.

What is claimed is:

1. A method for inhibiting proliferation of cancer cells that overexpress thymidine kinase 1 (TK1) in a mammal, wherein said TK1 is found on surfaces of said cells, said method comprising administering to said mammal a pharmaceutical composition comprising an anticancer agent comprising a humanized or fully human IgG monoclonal antibody that binds specifically to TK1, or a fragment thereof, wherein said pharmaceutical composition is administered to said mammal in an amount sufficient to inhibit proliferation of said cells, whereby proliferation of said cancer cells is inhibited.

2. The method of claim 1, wherein said monoclonal antibody is CB001.

3. The method of claim 1, wherein said pharmaceutical composition further comprises a second anti-cancer agent.

4. The method of claim 3, wherein said second anti-cancer agent is a nucleoside analog.

5. The method of claim 4, wherein the nucleoside analog is selected from the group consisting of 5' fluorouracil, fludarabine, cladribine, cytarabine, gemcitabine, capecitabine, troxacitabine, zidovudine/lamivudine (Combivir®), emtricitabine (Emtriva®), emtricitabine (Epivir®), zalcitabine (Hivid®) zidovudine (Retrovir®), abacavir/zidovudine/lamivudine (Trizivir®), didanosine (Videx®, VidexEC®), tenofovir disoproxil fumarate (Viread®), stavudine (Zerit®), and abacavir (Ziagen®).

6. The method of claim 1, wherein said antibody is conjugated to a cytotoxic agent.

7. The method of claim 6, wherein said cytotoxic agent is selected from the group consisting of pokeweed antiviral protein (PAP), ricin, abrin, gelonin, saporin, and alpha-sarcin.

8. The method of claim 1, wherein prior to administering said pharmaceutical composition, said mammal is treated with sufficient radiation at a tumor site to up-regulate TK1 expression at said site.

9. The method of claim 1, wherein said pharmaceutical composition further comprises a pharmaceutically acceptable liquid carrier adapted for parenteral administration.

10. The method of claim 9, wherein said liquid carrier comprises isotonic saline.

11. The method of claim 1 wherein said cancer cells are selected from the group consisting of lymphoma, breast, liver, cervical and pancreatic cancer cells.

* * * * *